United States Patent
Blew

(10) Patent No.: US 10,191,628 B1
(45) Date of Patent: Jan. 29, 2019

(54) ENVIRONMENT FOR DESIGNING A DYNAMIC MULTIMEDIA CONTENT PRESENTATION

(71) Applicant: Emmi Solutions, LLC, Chicago, IL (US)

(72) Inventor: Gregory A. Blew, Glen Ellyn, IL (US)

(73) Assignee: Emmi Solutions, LLC, Chicago, IL (US)

( * ) Notice: Subject to any disclaimer, the term of this patent is extended or adjusted under 35 U.S.C. 154(b) by 147 days.

(21) Appl. No.: 14/712,590

(22) Filed: May 14, 2015

Related U.S. Application Data

(60) Provisional application No. 62/084,439, filed on Nov. 25, 2014.

(51) Int. Cl.
*G06F 3/16* (2006.01)
*G06F 8/34* (2018.01)
*H04N 1/00* (2006.01)
*G06F 17/30* (2006.01)
*H04L 29/08* (2006.01)
(Continued)

(52) U.S. Cl.
CPC ........ *G06F 3/04842* (2013.01); *G06F 3/0482* (2013.01); *G06F 3/04847* (2013.01); *G06F 3/167* (2013.01); *H04L 67/10* (2013.01); *G06F 3/0487* (2013.01); *G06F 8/34* (2013.01); *G06F 17/30056* (2013.01); *H04N 1/00198* (2013.01)

(58) Field of Classification Search
CPC .. G06F 3/0482; G06F 3/04842; G06F 3/0487; G06F 3/167; G06F 8/34; G06F 17/30056; H04N 1/00198; H04L 67/10
See application file for complete search history.

(56) References Cited

U.S. PATENT DOCUMENTS 5,119,474 A * 6/1992 Beitel ............... G06F 17/30017
707/E17.009
6,031,529 A * 2/2000 Migos ................... G06F 3/0481
715/783
(Continued)

OTHER PUBLICATIONS

Adobe Developer Connection, "Creating your first Flash Professional CS5 document," (2010). . . Retrieved from the Internet on Mar. 10, 2015: <URL:https://adobe.com/devnet/flash/articles/flash_cs5_createfla.html> (2010).
(Continued)

*Primary Examiner* — Eric J. Bycer
(74) *Attorney, Agent, or Firm* — Marshall, Gerstein & Borun LLP; Randall G. Rueth

(57) ABSTRACT

According to an embodiment, when authoring an IMP, a designer may utilize an authoring tool to edit the visual and audio content associated with particular nodes. Further, in an embodiment, a designer may utilize an authoring tool to manipulate blocks corresponding to nodes of the IMP. For example, the authoring tool may include a library of stencils that the designer can utilize to create blocks corresponding to nodes of the IMP. In an embodiment, a designer may link the blocks to create a flow or tree establishing an ordered relationship between the blocks. A set of rules and/or facts may be generated based on the blocks and the designed flow. During IMP presentation, a rules engine may operate to activate nodes of the IMP based on the generated rules and/or facts.

31 Claims, 10 Drawing Sheets

(51) Int. Cl.
*G06F 3/0482* (2013.01)
*G06F 3/0484* (2013.01)
*G06F 3/0487* (2013.01)

(56) References Cited

U.S. PATENT DOCUMENTS

| | | | |
|---|---|---|---|
| 6,248,946 B1 | 6/2001 | Dwek | |
| 6,484,189 B1* | 11/2002 | Gerlach, Jr. | G06F 8/34 |
| | | | 715/201 |
| 6,567,829 B1 | 5/2003 | Ter Horst et al. | |
| 7,734,705 B1 | 6/2010 | Wheeler, Jr. et al. | |
| 8,214,518 B1 | 7/2012 | Bertz | |
| 8,838,748 B2 | 9/2014 | Nair et al. | |
| 9,705,754 B2 | 7/2017 | Crowder et al. | |
| 2002/0010759 A1 | 1/2002 | Hitson et al. | |
| 2002/0070956 A1* | 6/2002 | Chan | G06N 5/00 |
| | | | 715/714 |
| 2002/0083187 A1 | 6/2002 | Sim et al. | |
| 2004/0117839 A1 | 6/2004 | Watson et al. | |
| 2004/0122539 A1 | 6/2004 | Ainsworth | |
| 2005/0097008 A1* | 5/2005 | Ehring | G06F 17/211 |
| | | | 715/205 |
| 2005/0251731 A1* | 11/2005 | Valderas | G06F 9/543 |
| | | | 715/203 |
| 2006/0056388 A1* | 3/2006 | Livingood | H04L 41/12 |
| | | | 370/352 |
| 2007/0089100 A1* | 4/2007 | Morris | G06F 8/34 |
| | | | 717/139 |
| 2008/0065977 A1* | 3/2008 | Gottlieb | G06F 8/34 |
| | | | 715/203 |
| 2008/0098319 A1 | 4/2008 | Lucas | |
| 2008/0103371 A1 | 5/2008 | Rosenblum et al. | |
| 2008/0140719 A1 | 6/2008 | Chaney et al. | |
| 2009/0327895 A1 | 12/2009 | Bailloux et al. | |
| 2010/0180011 A1 | 7/2010 | Sood et al. | |
| 2011/0161409 A1 | 6/2011 | Nair et al. | |
| 2014/0244749 A1 | 8/2014 | Martin et al. | |
| 2014/0282013 A1* | 9/2014 | Amijee | G06F 17/30056 |
| | | | 715/732 |
| 2014/0344453 A1 | 11/2014 | Varney et al. | |
| 2015/0309695 A1* | 10/2015 | Sannandeji | G06F 8/34 |
| | | | 715/763 |

OTHER PUBLICATIONS

U.S. Appl. No. 14/695,542, filed Apr. 24, 2015, titled "Dynamic Management, Assembly, and Presentation of Web-Based Content".
U.S. Appl. No. 14/732,246, filed Jun. 5, 2015, titled "Multiple Delivery Channels for a Dynamic Multimedia Content Presentation".

* cited by examiner

ENVIRONMENT FOR DESIGNING A DYNAMIC MULTIMEDIA CONTENT PRESENTATION

CROSS-REFERENCE TO RELATED APPLICATION

This application claims priority to and benefit of U.S. Provisional Application Ser. No. 62/084,439, which was filed on Nov. 25, 2014 and is titled "Environment for Designing a Dynamic Multimedia Content Presentation," the entire disclosure of which is expressly incorporated herein by reference.

TECHNICAL FIELD

The present disclosure generally relates to dynamic network-based multimedia content presentations.

BACKGROUND

In a typical multimedia presentation, video, audio, and/or text may be presented to an end-user. Tools for creating such multimedia presentation generally create a file (e.g., an MP4 file or a SWF file) that can be transmitted to a client device so that the client device can play the multimedia content encoded to the file.

SUMMARY

According to an embodiment, a designer may utilize an authoring tool to design and/or edit an interactive multimedia pack (IMP). Generally speaking, an IMP is an application or collection of applications for presenting multimedia content to an end-user via an end-user device. The IMP may include various nodes that may be activated or executed to present a certain subset of the multimedia content associated with the IMP.

According to an embodiment, when authoring an IMP, a designer may utilize an authoring tool to edit the visual and audio content associated with particular nodes. Further, in an embodiment, a designer may utilize an authoring tool to manipulate graphical blocks corresponding to nodes of the IMP. For example, the authoring tool may provide a library of stencils that the designer can utilize to create blocks corresponding to nodes of the IMP. In an embodiment, a designer may link the blocks to create a flow or tree establishing an ordered relationship between the blocks. A set of rules and/or facts may be generated based on the blocks and the designed flow. During IMP presentation, a rules engine may operate to activate nodes of the IMP based on the generated rules and/or facts.

DETAILED DESCRIPTION

I. Overview

Figure 1A:
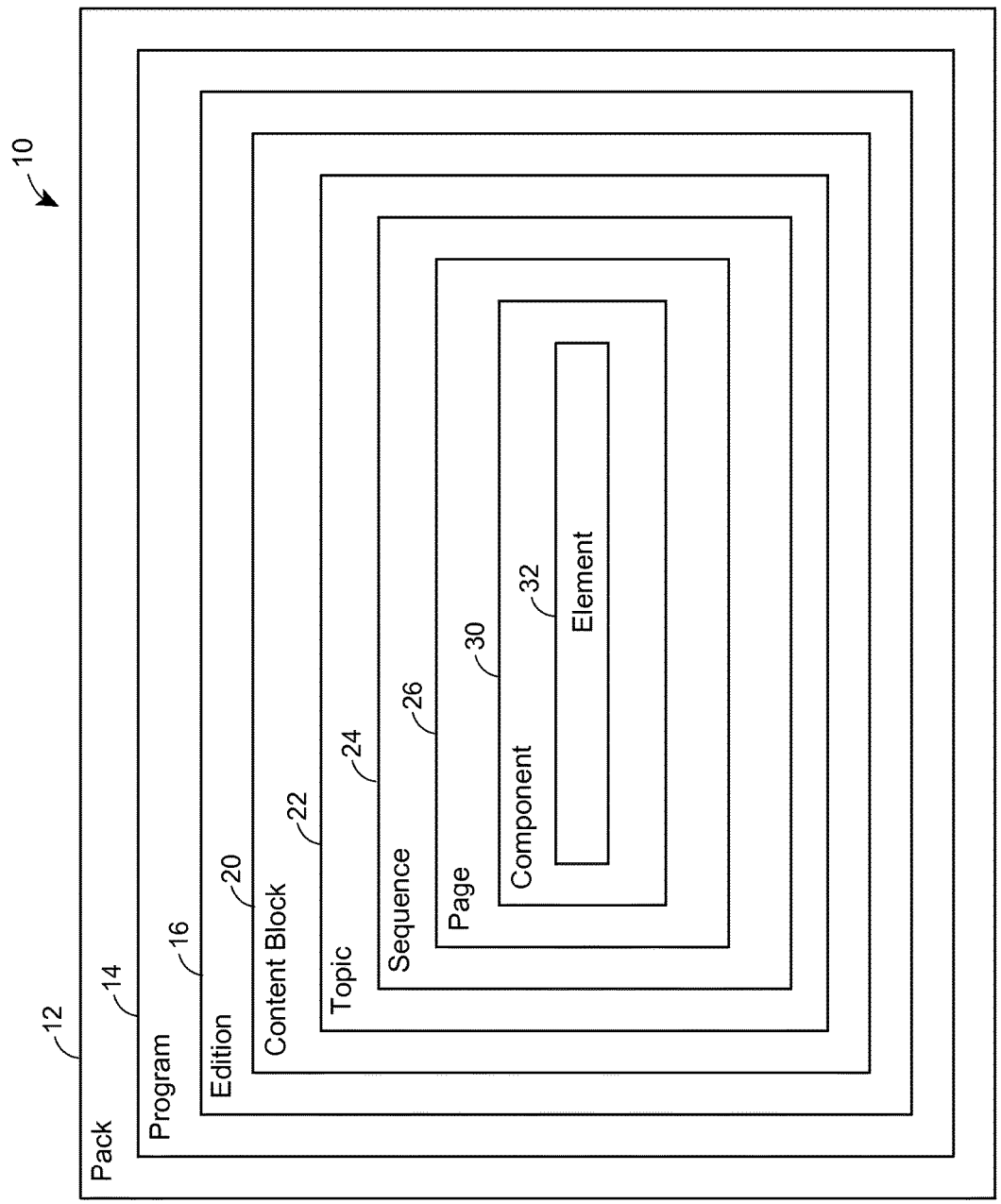
FIG. 1A depicts an example hierarchy for an IMP, according to an embodiment.

Generally speaking, an interactive media pack (IMP) is designed to present multimedia content to a user (generally referred to as an "end-user") via an end-user device (sometimes referred to as a "client device"). The IMP may include various nodes that may be activated or executed to present a certain sub-set of the multimedia content associated with the IMP. The IMP may be interactive in nature, allowing an end-user to interact with the presented content. For example, the IMP may prompt the end-user to answer various questions. Further, the IMP may be dynamic in nature. For example, an IMP may include various nodes that may be selectively activated or executed, where each node, if and when activated, may present to the end-user a certain subset of the multimedia content associated with the IMP. Which nodes are activated, and/or the order in which the nodes are activated, may be determined, in whole or in part, during run-time. Accordingly, the particular sequence in which the multimedia content is presented to a user may not be known prior to the IMP being initiated.

The conditional logic used to decide which nodes of an IMP should be next activated may be embodied by "rules." These rules may take any of a number of forms, but generally speaking, may be any information or data that can be referenced for determining what node should be next activated. In an embodiment, one or more of the rules may reside at a third party system. Further, the one or more rules may be implemented, in whole or in part, by a third party system. In other embodiments, none of the rules reside at a third party system, and/or are not implemented by third party systems. To illustrate, the rules may be implemented by a rules engine. Generally speaking, a rules engine is a system configured to select a next node to be activated, for example, according to the rules (i.e., according to logic embodied by the rules) and/or according to other data or information (e.g., "facts"). In an embodiment, the rules engine is implemented, in whole or in part, by a third party. In other embodiments, the rules engine is not implemented by a third party. Regardless of the exact manner of implementation, the rules engine may select a next node for activation according to the rules.

The rules may specify one or more conditions and a particular node to activate when these one or more conditions exists. The existence or non-existence of these conditions may depend on the existence or non-existence of one or more "facts." Thus, to evaluate each condition specified by the rules, the rules engine may access facts stored in a knowledge base and may determine the appropriate node(s) to activate, during run-time, by way of the rules operating on those facts. To illustrate, a rule may stipulate "activate Node X if today is a Tuesday." The condition "today is a Tuesday" depends on a fact: what day of the week "today" actually is. In such an example, the rules engine may access facts in the knowledge base to evaluate the condition "today is a Tuesday," and may activate Node X when the condition is true.

The facts may represent information that was previously provided by the end-user (e.g., in response to user prompts presented earlier within the IMP), and/or information that was collected from other sources (e.g., electronic medical records, patient registry software, prescription software, biometric devices worn by patients, etc.), for example.

The term "nodes," as used herein, may generally refer to units of content of any size or duration, or of variable size and/or duration, within an IMP, and/or to decision-points that connect other nodes within the IMP. At a high level, the nodes of the IMP can be understood as belonging to one of four categories: an output-node, an input-node, a decision-point-node, or a collection-node. Output-nodes generally represent a "page" to be displayed to an end-user via a display device. Each "page" may include one or more content assets. Examples of these content assets may include an audio content asset and/or a visual content asset (e.g., an image, video, animation, text, or some combination thereof). An input-node generally represents an input prompt to be displayed to an end-user (e.g., a pop-up box including a question and multiple potential answers that may be selected via radio buttons). A decision-point-node generally represents a decision-point within the IMP, where the rules engine may evaluate one or more conditions associated with the decision-point-node to determine a next action for the IMP (e.g., to determine which next node to activate). Finally, a collection-node represents a collection of nodes, and may specify a flow between one or more of its constituent nodes. A collection-node may include output-nodes, input-nodes, decision-point-nodes, and even other collection-nodes. Accordingly, the hierarchy and organization of an IMP can quickly become quite complex.

In an embodiment, a particular collection-node (i.e., a node that may include other nodes) may be referred by a name denoting a particular layer within the hierarchy of an IMP. For example, a particular collection-node may be referred to as a "program," "edition," "content block," "chapter," "topic," "sequence" depending on the overall configuration of the IMP and the level of hierarchy for the particular collection-node in question. As noted, an IMP and its nodes may be arranged according to various configurations or hierarchies, such as a flat configuration, or a hierarchy with nodes at multiple layers (e.g., nodes within nodes). For instance, nodes within one layer of an IMP may include different "programs" that broadly serve different purposes within the IMP (e.g., obtaining advanced directives, obtaining informed consent, facilitating decision-making with respect to a particular health condition, etc.), nodes within a lower layer of the IMP may include different "content blocks" or "chapters" that serve different, more specific purposes within programs (e.g., informing a patient/end-user about a specific subject or asking the patient a subset of questions associated with a subject, etc.), and nodes within a still lower layer of the IMP may include different "pages" that are to be displayed/presented to the end-user within the content blocks or chapters. One example hierarchy, including still more layers, is described below in Section II.

In some embodiments, the dynamic/selective activation (or non-activation) of nodes discussed above occurs within each of multiple hierarchy layers. Referring to the hierarchy examples above (IMP, program, content block, page), for instance, conditional logic may be applied at run-time to determine which page is to be presented next within a particular content block. Similarly, other conditional logic may be applied at run-time to determine which content block is to be presented next within a particular program. Each hierarchy layer may or may not be transparent to the end-user (e.g., depending on whether the presented content includes information that demarks the different nodes within each layer, such as program names, chapter titles, etc.).

Depending on the embodiment, the conditional logic within various layers of an IMP may be understood as a particular type (or category) of conditional logic. For example, the conditional logic may be embodied by rules that facilitate scheduling, and/or rules that facilitate conditional branching. Scheduling may involve activating a node or nodes (and potentially an order for said activation) based on one or more factors (e.g., events or triggers not necessarily expected to occur at any particular time). Conditional branching may involve evaluating conditions at a particular point during execution of an IMP (e.g., at an expected decision-point) to identify a next node for activation from multiple potential nodes. Facts or factors upon which rules for scheduling and/or conditional branching can be based may include, for example: what doctors prescribe to patients; temporal-based events based on schedule, such as reminder calls to watch a program, collect feedback, etc.; special rules and configurations by the hospital or clinic; chaining programs together for illnesses that are related; workflow automation in the context of the above and the extent to which other tasks integrate with other systems (e.g., call systems); information contained within (or derived from) end-user feedback that was provided in response to a user prompt presented earlier in a particular program; etc.

Generally, portions of an IMP may, in some embodiments, be presented to the end-user via one communication channel, or via multiple communication channels. Thus, an IMP may have collection-nodes (e.g., programs, sequences, etc.) designed for a particular communication channel (e.g., for presentation via web browser, text messaging, email, telephone, etc.). For example, a first program within a particular IMP may include multimedia content that is presented to the end-user via a web browser of the end-user's computing device, while a second program of the IMP may include a survey presented to the end-user via email (or via a telephone call using interactive voice response (IVR) technology, etc.).

In some instances, there may exist multiple "versions" of an IMP or of particular portions of an IMP (e.g., of particular programs, chapters, sequences, etc.). These versions may represent substantially the same information that needs to be presented to, or collected from, a user. For example, with reference to the previous example, the first and second program may each be understood as "versions" or "editions" of the same program. Each version may be designed for a particular communication channel. A "monitor" (e.g., implemented by a server) may track the progress of a particular IMP presentation, or of a particular portion of an IMP presentation (e.g., for a particular chapter of an IMP, a sequence of an IMP, a program of an IMP, etc.). The monitor may store progress data representing this progress. This progress data may be referenced to enable transitions between "versions" of an IMP without losing progress in the presentation. For example, in some instances, the progress data may be referenced when presentation of a first version is paused or stopped to "resume" presentation of a second version at a point corresponding to the point where the first version was paused or stopped. In other embodiments, the entire IMP may be presented to the end-user via a single communication channel.

An authoring tool may enable a designer to design and/or edit an IMP. In particular, a designer may utilize an authoring tool to edit the visual and audio content associated with particular nodes. In an embodiment, an authoring tool may include a first interface for editing visual content and a second interface for editing audio content. The first and second interface may exhibit interconnected behavior in some embodiments. For example, when a designer begins working on a particular node in the first interface, the second interface may automatically display relevant information for editing that particular node in the second interface as well (and vice versa).

Further, in an embodiment, a designer may utilize the authoring tool to manipulate graphical blocks corresponding to nodes of the IMP. The authoring tool may provide a third interface for manipulating these graphical blocks. The designer may utilize such an interface to link blocks to create a flow or tree establishing an ordered relationship between the blocks. A set of rules and/or facts may be generated based on the blocks and the designed flow. The third interface may exhibit interconnected behavior with respect to the first and second interface. For example, when a designer begins working on a particular node in the first or second interface, the third interface may display a block corresponding to that particular node, enabling the designer to (i) determine how that particular node relates to other nodes in the flow of the IMP, and (ii) establish a flow between the particular node and the other nodes in the flow of the IMP.

When the IMP is presented, a rules engine may operate to activate nodes of the IMP based on the generated rules and/or facts. When activated, these nodes may cause an end-user device to display certain multimedia content associated with the node.

An authoring tool may be utilized to allow artists, designers, and/or the production team to author programs easily. Program authors (who may also be referred to as 'designers') may drag and drop a sequence of steps (which may be referred to as 'stencils' or 'blocks' below) in a flowchart type network displayed in an authoring tool. Each block may represent a node (e.g., "chapter" or "page") in an IMP flow.

II. Example IMP Hierarchy

FIG. 1A depicts an example hierarchy 10 for an IMP 12, according to an embodiment. The hierarchy 10 includes a program layer 14 with one or more programs of the IMP 12, an edition layer 16 with one or more editions per program, a content block layer 20 with one or more content blocks per edition, a topic layer 22 with one or more topics per content block, a sequence layer 24 with one or more sequences per topic, a page layer 26 with one or more pages per sequence, a component layer 30 with one or more components per sequence, and an element layer 32 with one or more elements per component.

It will be understood that the example hierarchy 10 is a single example hierarchy that an IMP may have in an embodiment, and that an IMP may have a hierarchy different than the hierarchy 10. For example, depending on the embodiment, an IMP may have none of the higher levels of hierarchy. To illustrate, in some instances an IMP may include one or more nodes representing pages, but none of the other collection-nodes displayed in FIG. 1A (i.e., no programs, editions, content blocks, topics, or sequences). In other embodiments, an IMP may include layers of hierarchy above the page layer. In short, an IMP may include any combination of collection-nodes, some or all of which may include other collection-nodes. Thus, the hierarchy of an IMP may be understood as depending on the different collection-nodes existing within an IMP, and the extent to which these collection-nodes include other collection-nodes.

Generally, the IMP 12 may be directed to any type of subject matter, and may serve any type of purpose or purposes relating to that subject matter. For example, the IMP 12 may be designed to facilitate steps of a clinical flow associated with a particular type of medical treatment, therapy or condition. Within the program layer 14, each program may have a particular high-level function, such as obtaining and documenting informed consent (e.g., prior to a surgical procedure for the end-user/patient), obtaining and documenting an advanced directive (e.g., to specify what action should be taken if the end-user/patient is unable to make informed decisions due to health/incapacity issues), providing support for treatment and/or medication decisions, a mix of two or more such functions, etc.

Each of one, some or all of the programs within the program layer 14 may be associated with multiple editions in the edition layer 16. Each edition within a particular program may correspond to a different type of communication channel that is used to convey the program to the end-user. A "communication channel" for a particular edition may refer to the file format of the program content, the file format of instructions specifying the structure and presentation of the program content, and/or the type of end-user device needed to present the program content, for example. To provide some more specific examples, a first edition may correspond to an HTML5 edition of the program intended for presentation on a device with an HTML5-capable browser, a second edition may correspond to an Adobe Flash™ version of the program intended for presentation on a laptop or desktop computer, a third edition may correspond to an SMS text version of the program intended for presentation on a mobile phone device, a fourth edition may correspond to an IVR version of the program intended for presentation via a mobile or landline phone, and so on. Of course, some types of editions/communication channels may be unsuitable for particular programs (e.g., an IVR edition may be unsuitable for a program that heavily relies on video content), and/or some or all programs within the program layer 14 may only be associated with a single edition.

Each content block within the content block layer 20 may have a particular function, such as providing background information to the end-user, collecting information from the end-user (e.g., demographic information, information reflecting a self-assessment of symptoms, etc.), providing results to the end-user (e.g., based on information that the end-user entered earlier in the program), taking a particular action (e.g., scheduling a follow-up appointment, providing or setting up a reminder, sending results to healthcare professionals, etc.), a mix of two of more such functions, or any other suitable function.

Each topic within the topic layer 22 may have a more specific function within its respective/parent content block, such as providing a particular subset of background information to the end-user, collecting a particular subset of information from the end-user, etc. In some embodiments, topics may be the only divisions of an IMP that are noticeable to the end-user, with all other layers of the hierarchy 10 being transparent to the end-user.

Each sequence of the sequence layer 24 may contain an animation, a series of images and/or text, and/or other temporally-varying visual and/or audio content. A single sequence may contain a number of pages from the page layer 26, where each page arranges one or more components in the component layer 30 according to a layout specific to that page. In some embodiments, the layout of each page is dependent on the display capabilities of the end-user device (e.g., the aspect ratio of the display screen). Each component of a page may be a collection of one or more visual and/or audio elements within the element layer 32 (e.g., blocks of text, snippets of audio or video, etc.).

Some of the nodes/units within one or more of the layers of the example hierarchy 10 may be reusable. For example, a content management system may store a number of different topics, each of which can be retrieved and plugged into different content blocks and/or different IMPs. As another example, the content management system may store a number of different content blocks, each of which can be retrieved and plugged into different programs and/or different IMPs.

It is understood that, in other embodiments/implementations, the hierarchy 10 may include more, fewer and/or different layers than those shown in FIG. 1A. Moreover, a single IMP may be viewed as having multiple different hierarchical configurations (e.g., by grouping the content of the IMP in various different ways).

III. Example System for IMP Creation and Presentation

Figure 1B:
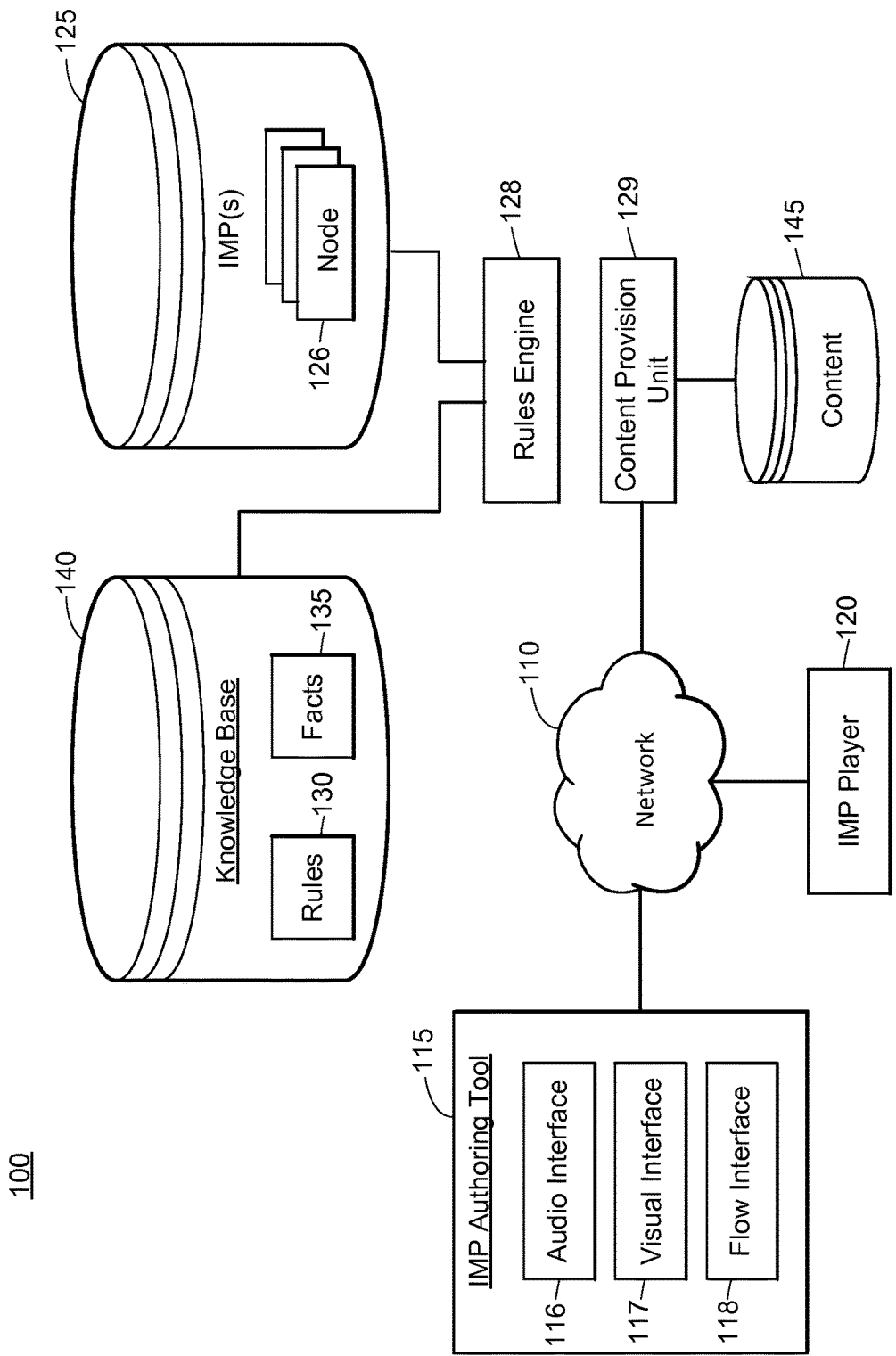
FIG. 1B illustrates a block diagram of an example system for creating and presenting IMP(s) according to an embodiment.

FIG. 1B illustrates a block diagram of an example system 100 for creating and presenting IMP(s) 125.

In an embodiment, the system 100 includes a network 110, an IMP Authoring Tool 115, an IMP Player 120, a rules engine 128, a content provision unit 129, a database storing data for one or more IMPs 125, a knowledge base 140, and a content database 145. The knowledge base 140 may include one or more databases storing rules 130 and facts 135. The data for the one or more IMPs 125 may include data for one or more nodes 126 of the IMP(s) 125.

Each of the IMP Authoring Tool 115, IMP Player 120, the rules engine 128, and the content provision unit 129 may reside on a computing device. For example, the rules engine 128 and the content provision unit 129 may reside on the servers 620 shown in FIG. 6. In an embodiment, the rules engine 128 and content provision unit 129 are each implemented by a different server. In another embodiment, the rules engine 128 and content provision unit 129 are both implemented by a single server. Each of the IMP Authoring Tool 115, IMP Player 120, the rules engine 128, and the content provision unit 129 may be coupled to the network 110. The network 110 may be any suitable network, including wireless and/or wired links.

A. Presentation of the IMP 125

The IMP 125 may be presented at the IMP Player 120 based on data received from the rules engine 128 and/or the content provision unit 129. The information to be presented and/or collected during presentation of the IMP 125 may depend on the rules 130 and/or facts 135 that exist during runtime.

1. The IMP Player 120, Rules Engine 128 and Content Provision Unit 129

The IMP Player 120 is a tool for presenting the IMP 125. Generally speaking, the IMP Player 120 may be one or more instructions, routines, modules, processes, services, programs, and/or applications that when executed by a processor cause a display device to present a graphical user-interface (GUI) to a user ("end-user) to enable the end-user to "play" the IMP 125.

The rules engine 128 is a tool for identifying one or more next nodes of the IMP 125 to be presented during run-time. Generally speaking, the rules engine 128 may be one or more instructions, routines, modules, processes, services, programs, and/or applications that when executed cause a processor to evaluate one or more rules 130 and/or facts 135 in the knowledge base 140 and to identify a next node or nodes 126 for presentation.

The content provision unit 129 is a tool for content delivery. Generally speaking, the content provision unit 129 may be one or more instructions, routines, modules, processes, services, programs, and/or applications that when executed cause a processor to retrieve content assets from the content database 145 and to transmit the retrieved content assets to the IMP Player 120.

Generally speaking, the nodes 126 are data corresponding to particular subsections or modular portions of the IMP 125 that may be presented via the IMP Player 120. The nodes 126 (or node data 126) may include executable instructions or routines representing these particular subsections or modular portions of the IMP 125. Each node 126 generally represents an output to be displayed via a GUI of the IMP Player 120, (e.g., a page including one or more multimedia content assets), an input prompt to be displayed via a GUI of the IMP Player 120, or a decision-point at which point the rules engine 128 will select a next node 126 for activation from multiple potential next nodes. The node data 126 may include HTML5 instructions that specify, for each node, the content asset(s) that is/are to be presented, as well as the presentation of that content. For example, the HTML5 instructions may specify the layout(s), font(s), and/or one or more other characteristics for each content asset within each presented page/screen within a given node.

In example operation, the IMP Player 120 presents multimedia content to the end-user according to the nodes 126 of the IMP 125, each of which may reference or include particular multimedia content. The particular nodes 126 to be played, and the order in which they are played, may be determined by the rules engine 128.

The rules engine 128 may evaluate one or more of the rules 130 and/or facts 135 in the knowledge base 140, and may identify a next node or nodes 126 for presentation based on that evaluation. In an embodiment, the rules engine 128 may evaluate a rule 130, but not a fact. For example, in an embodiment, a rule 130 may simply stipulate "Activate Node Z after Node Y." The multimedia content associated with each node 126 may be referred to as a "content asset." The content assets may be stored at the content database 145, and may be retrieved by the content provision unit 129 and transmitted to the IMP Player 120. An example content asset may be or may include an element in the element layer 32 shown in FIG. 1A, and/or a component in the component layer 30 shown in FIG. 1A.

In an embodiment, the rules engine 128 may transmit the identity of the identified next node 126 to the IMP Player 120. The content provision unit 129 may provide the content asset(s) associated with the identified next node 126, alone or in a group with the content assets of one or more other nodes 126. The content provision unit 129 may send content only upon request from the IMP Player 120, or without waiting for a request, in different embodiments. In an embodiment, the rules engine 128 may also transmit the identity of the identified next node 126 to the content provision unit 129. The content provision unit 129 may then reference the node data 126 to identify the appropriate content assets associated with the identified next node 126, and may transmit the appropriate content assets to the IMP Player 120. Alternatively, the rules engine 128 may reference the node data 126 to identify the appropriate content assets associated with the identified next node 126, and may communicate with the content provision unit 129 to cause the content provision unit 129 to transmit the appropriate content assets to the IMP Player 120.

In some instances, some of the nodes 126 are organized into groups that may be referred to as "collection-nodes." These collection-nodes may be referred to as "programs," "editions," "content blocks," "chapters," "topics," or "sequences" depending on the overall configuration of the IMP 125 and the level of hierarchy for the particular collection-node in question. The order in which the IMP Player 120 presents the multimedia content associated with the nodes 126 may be determined based on the rules 130 and facts 135 in the knowledge base 140.

2. The Rules 130 and Facts 135

When the IMP 125 is presented via the IMP Player 120, the nodes 126 may be activated according to an order determined based on the rules 130 and/or facts 135 (e.g., determined by the rules engine 128). The rules 130 and/or facts 135 may be defined according to user input entered via the IMP Authoring Tool 115 (e.g., a designer creating rules and/or specifying facts) and/or via the IMP Player 120 (e.g., an end-user providing an answer to a query that is then inserted into the knowledge base 140 as a new fact).

The defined rules 130 may specify various conditions for determining which of the potential next nodes 126 should be activated. The rules engine 128 may analyze these rules 130 and facts 135 to determine which condition(s) are met (and thus to determine which of the multiple potential next nodes 126 should be activated).

As noted, during presentation of the IMP 125, the rules engine 128 may select a next node 126 for activation based on the rules 130 and the facts 135. A fact 135 is generally a variable or attribute value. For example, a fact 135 may indicate the existence of various diseases or disorders (e.g., diabetes, heart disease, cancer, etc.) or identify demographic information for a person (e.g., gender, blood type, height, weight, age, etc.).

Generally, each rule 130 specifies a condition and an action. When the rules engine 128 fires, it evaluates one or more rules 130 and one or more facts 135 to determine whether the condition(s) specified by the one or more rules 130 are true. If a condition is true, the corresponding action is initiated. The action may specify a node 126 or program (e.g., a collection of nodes 126) to activate. For example, a rule 130 may specify a condition (e.g., a person is a smoker) and an action to initiate if the condition is true (e.g., initiate a 'stop smoking' node 126). The rules engine 128 generally evaluates a rule 130 based on the facts 135 (e.g., a 'smoker' variable may exist to indicate whether a particular person is a smoker). In some instances, the action may specify a new fact 135 to insert into the knowledge base 140. For example, if a needed fact 135 does not exist or has not been defined, an input prompt may be activated to request user-input that can be used to define a new fact 135.

The rules 130 and facts 135 may be created or defined based on information from any of a number of data sources. For example, facts may be added or updated using data from electronic medical record (EMR) software or systems (e.g., for facts relating to patient encounter and/or diagnosis data), data from customer and/or partner relation management (CRM or PRM) software or systems (e.g., for facts relating to when a patient was contacted, and why), data from analytics vendors, software or systems (e.g., for facts relating to patient populations/cohorts), data from patient registry software or systems (e.g., for facts relating to patient scheduling), and/or data from prescription software or systems (e.g., for facts relating to whether a patient has, or has filled, a particular prescription). As another example, facts may be added or updated using data from personal and/or bedside biometric or other medical devices. For instance, one or more facts relating to the vital signs of a patient may be periodically updated based on signals from a heart monitor worn by the patient.

Further, rules 130 and/or facts 135 may be created or defined based on information provided by an end-user. For example, a fact relating to pain severity level may be set to a value between 1 and 10 based on a value that was entered by the end-user when prompted to rate his or her pain level on a scale of 1 to 10. In some embodiments and/or scenarios, facts may be derived from, but different than, information entered by the end-user. For example, a knowledge base may store the fact "pain=high" if the end-user entered a pain level value between 6 and 10, or the fact "pain=low" if the end-user entered a pain level value between 1 and 5. The techniques utilized to gather information from an end-user may vary significantly. For example, in an embodiment, B. IMP Authoring Tool 115 and Creation of the IMP 125

The IMP Authoring Tool 115 may be utilized to generate or define the rules 130 and/or facts 135. Generally speaking, the IMP Authoring Tool 115 may be one or more instructions, routines, modules, processes, services, programs, and/or applications that when executed by a processor cause a display device to present one or more graphical user-interfaces (GUIs) to enable a user of the IMP Authoring Tool 115 ("designer") to create and/or manipulate (e.g., via user-input) the design of the IMP 125.

The IMP Authoring Tool 115 may include one or more components or parts: an audio interface 116, a visual interface 117, and/or a flow interface 118. Generally speaking, the audio interface 116 and visual interface 117 enable a designer to select or define content that will be presented when one or more particular nodes 126 of the IMP 125 are presented during presentation of the IMP 125. By comparison, the flow interface 118 enables a designer to define a flow between nodes 126 of the IMP 125, wherein the flow generally corresponds to an order for presenting the nodes 126 during presentation of the IMP 125. Accordingly, the flow interface 118 might be considered a "high-level" editor when compared to the audio interface 116 and visual interface 117.

1. Audio Interface 116

The audio interface 116 may be displayed at a display device to a designer. In short, the audio interface 116 enables the designer to define or select audio to be presented when a particular node 126 or set of nodes 126 of the IMP 125 is presented to an end-user during presentation of the IMP 125. For example, a designer may utilize the audio interface 116 to define particular audio to be presented (e.g., via a speaker) when a particular page of the IMP 125 is presented.

In an embodiment, the displayed audio interface 116 includes a text field for defining audio to be presented when a particular page is presented. The designer may enter text in the text field. The provided text may be converted to audio using a text-to-speech tool. In some instances, a person might record audio of himself or herself reading the provided text. In either event, the audio may be stored to memory as associated with the particular page.

In an embodiment, the audio interface 116 includes an input element (e.g., a button) that the designer may interact with to cause the IMP Authoring Tool 115 to record audio. The designer might then record (e.g., via a microphone) audio that he or she desires to be presented with the particular page. Such an embodiment may not require text entry.

In some embodiments, the audio interface 116 displays multiple audio files from which the designer can choose. Regardless of how the audio has been defined (i.e., whether defined via text entry, audio recording, file selection, or some other means of audio selection/definition), the IMP Authoring Tool 115 may store to memory data for the particular page (e.g., as node data 126) referencing the defined audio, so that the stored data may be later referenced to identify the defined audio as associated with the particular page the designer was editing via the audio interface 116.

2. Visual Interface 117

The visual interface 117 may be presented at a display device to a designer. The visual interface 117 enables the designer to define or select visual elements to be displayed when a particular node 126 or set of nodes 126 of the IMP 125 is presented to an end-user during presentation of the IMP 125. For example, the designer may utilize the visual interface 117 to define particular visuals (e.g., text and/or images) to be presented (e.g., via a display device) when a particular page of the IMP 125 is presented.

In an embodiment, the displayed visual interface 117 includes a "design area" (which may be referred to as a "visual design area") where a designer may place visual elements to be displayed when a particular page is displayed. In some instances, the visual interface 117 may include a library area where various images or image identifiers are displayed. These images or image identifiers may be "dragged and dropped" into the design area. In some instances, the visual interface 117 may include an input element (e.g., a button, toolbar menu, or some other interactive graphic element) that a designer may interact with to activate the library (i.e., to cause the visual interface 117 to display the library). In any event, the IMP Authoring Tool 115 may store to memory data for the particular page (e.g., as node data 126) that references the visual element(s) that have been placed in the design area, so that the stored data may be later referenced to identify selected visual elements as associated with the particular page the designer was editing via the visual interface 117.

3. Flow Interface 118

The flow interface 118 may be presented at a display device to a designer. The flow interface 118 enables the designer to define or select a flow between nodes 126 of the IMP 125. In short, this flow defines the particular nodes 126 to be presented (or potentially presented) during presentation of the IMP 125, as well as an order or potential order(s) in which the nodes 126 are to be presented. While the exact determination regarding node-selection and order of presentation may not be known until run-time (because node-selection and order of presentation may depend on conditions and facts that are not evaluated until run-time), the flow defines a broad structure or outline for presentation of the IMP 125.

In an embodiment, the displayed flow interface 118 includes a "design area" (which may be referred to as a "flow design area") where a designer may place blocks or icons representing nodes 126 of the IMP 125, which may include, e.g., output-nodes, input-nodes, decision-point-nodes (corresponding to conditions to be evaluated at run-time), and/or collection-nodes. Further, a designer may utilize a design area of the flow interface 118 to define connections between the blocks or icons representing the nodes 126. These placed blocks or icons, and the connections between them, generally define a flow. The defined flow may be used to add, edit, and/or delete rules 130 and/or facts 135 in the knowledge base 140.

Accordingly, using the flow interface 118, the designer can add, edit, and/or delete rules 130 and/or facts 135 that will be utilized by the rules engine 128 during runtime to identify a next node 126 for execution. The designer can make these changes by adding, removing, or editing node icons or blocks in a "design area" of the flow interface 118. Each created block corresponds to a particular node 126. The node icons or blocks may be pulled from a library in the IMP Authoring Tool 115. Further, the designer may link the blocks, creating a block tree. The rules 130 may be created/defined based on the blocks and block tree designed by the designer. Accordingly, the IMP Authoring Tool 115 enables the designer to create a sequence of linked blocks, representing a hierarchy or potential "flow" of nodes 126 to be activated when the IMP 125 is presented via the IMP Player 120.

In some instances, the flow interface 118 displayed by the IMP Authoring Tool 115 may include a library of preconfigured blocks, which may be referred to as "stencils." A stencil may be understood as template block. A stencil may be placed in the design area to create a block from the stencil. In some instances, the designer may assign certain attributes or values to the block (e.g., specifying particular multimedia content that will be presented when the node 126 corresponding to the created block is activated). For example, the library may include a radio-button user-input stencil. The designer may drag the stencil into a "design area," where the designer may bind various attributes and/or attribute values to the stencil to define a particular node. For example, the designer may specify particular text that defines the question that will be asked when the node is activated. Similarly, the designer may specify an attribute that will be defined based on the input provided by the end-user.

As another example, a designer using the IMP Authoring Tool 115 may create a block corresponding to a decision node 126 that has two branches leading to first and second potential next blocks. The designer may define a condition (e.g., variable XYZ has the value 'TRUE') for a rule 130, where the branches stemming from the created block represent the actions for the rule 130. Thus, when the IMP 125 is initiated for presentation to an end-user and the decision node 126 corresponding to the created block is activated, the rules engine 128 may (i) initiate a first action (e.g., a first node 126 is activated) when the condition is true (e.g., XYZ='TRUE'); and (ii) initiate a second action (e.g., a second node 126 is activated) when the condition is false (e.g., XYZ='FALSE' or null).

In some instances, the designer may create a block so that an input prompt is generated and the condition of the corresponding rule 130 depends on the end-user's input (which may also be inserted into the knowledge base 140 as a new fact 135). In other words, the selection of a next node 126 for activation may depend on end-user input. It will be understood that the above examples are illustrative and that the IMP Authoring Tool 115 may be used to define a rule 130 with other conditions and actions.

In some instances, the designer may designate a particular flow-definition to be a collection-node. That is, the designer may specify a particular level of hierarchy within the IMP 125 for a flow-definition created in the flow interface 118. As an example, the designer may create multiple "editions," where each edition represents substantially the same goal regarding information communicated to, and collected from, an end-user. To further illustrate, a designer may create a first flow definition for an edition meant to be presented via a client device that is a desktop computer. The designer may create a second flow definition for an edition meant to be presented via a client devices that is a mobile phone or tablet. The rules engine 128 may determine which edition to present to the client device based on the client device type. In some instances, a designer may create a flow-definition meant to be presented to via text messages to a client device. In such instances, the flow-definition may consist of pages including text and/or images formatted for presentation via text messaging (e.g., the images may be a lower resolution, and thus smaller in file size).

In short, it may be said that the IMP Authoring Tool 115 enables a designer to "program" an IMP 125. Importantly, such "programming" does not require a great deal of experience or skill, and thus enables non-programmers to "program" an IMP 125. After the IMP 125 has been edited or created, its contents may be stored at a memory device. In an embodiment, the contents of the IMP 125 are stored at a database or memory device accessible via the network 110. In some embodiments, one or more servers may provide the contents of the IMP 125 to an end-user device via the network 110.

4. Interconnectivity Between the Audio Interface 116, Visual Interface 117, and Flow Interface 118

In an embodiment, the audio interface 116, visual interface 117, and flow interface 118 may exhibit interconnected behavior. For example, when a designer has finished working on a first page in the audio interface 116, and begins working on a second page in the audio interface 116, the visual interface 117 may automatically display the visuals associated with the second page. Thus, the IMP Authoring Tool 115 enables the designer to easily switch back and forth between editing the audio content assets and the visual content assets of the second page. A similar procedure may occur when the designer stops working on a first page in the visual interface 117 and begins working on a second page in the visual interface 117. In short, the IMP Authoring Tool 115 may anticipate that the designer will want to edit the visual content assets associated with a particular page if he or she is editing the audio content assets associated with that particular page, and vice versa.

In an embodiment, when a designer is editing a particular page in the audio interface 116 or visual interface 117, the flow interface 118 may highlight a block or icon representing the particular page that is being edited, enabling the designer to easily determine how the particular page relates to other nodes in the flow of the IMP 125. Similarly, when a designer has selected a block in the flow interface 118 representing a particular page, the audio interface 116 and/or visual interface 117 may display or list the visual and/or audio information for that particular page. In short, the IMP 125 may anticipate that when the designer is editing the audio or visual content assets associated with a particular page, the designer may want to define how or when that particular page will be presented during presentation of the IMP 125. Similarly, when a designer is placing a block representing a particular page within a flow in the flow interface 118, the designer may benefit from being able to easily determine (and potentially edit) what audio and visual content assets are associated with that particular page.

In an embodiment, when a designer creates a new page in the audio interface 116, a new template may be created for editing the visuals of the new page in the visual interface 117 (and the visual interface 117 may automatically display that template in the design area of the visual interface 117). Similarly, when a designer creates a new page in the visual interface 117, a new page may be listed in the audio interface 116, enabling the designer to quickly and easily edit the audio for the newly created page.

Further, in some embodiments, when a new page is created in the audio interface 116 or the visual interface 117, a block representing the new page may be automatically added to the design area of the flow interface 118, enabling the designer to quickly and easily integrate the new page into the overall flow of the IMP 125. Similarly, when a designer creates a new page in the flow interface 118, the audio interface 116 and visual interface 117 may automatically display or list information for the newly created page, enabling the author to easily edit the audio content assets and visual content assets of the newly created page in the audio interface 116 and visual interface 117, respectively.

The audio interface 116 and/or the visual interface 117 may include an indicator corresponding to the flow of the IMP 125 that might otherwise be displayed via the flow interface 118. For example, the audio interface 116 and/or visual interface 117 may display all or some of the flow to which the page currently being edited belongs. In an embodiment, the audio interface 116 and/or visual interface 117 may display the next node (or next potential nodes) in the flow following the node corresponding to the current page being edited. Similarly, in an embodiment, the audio interface 116 and/or visual interface 117 may display the previous node in the flow. In an embodiment, the next node and/or previous node may be displayed via an interactive element that the user can activate (e.g., by touching via a touchscreen or clicking via a mouse) to cause the audio interface 116 or visual interface 117 to display information for the next/previous node, enabling the user to edit the corresponding page.

IV. Example Displays Provided by the IMP Authoring Tool 115

FIGS. 2-5 depict example displays that may be provided by a display device during operation of the IMP Authoring Tool 115, according to an embodiment. In an embodiment, each of the displays 200-500 may be displayed via the controller 610 and display device 637 shown in FIG. 6.

A. Display 200 of the Audio Interface 116 and Visual Interface 117

Figure 2:
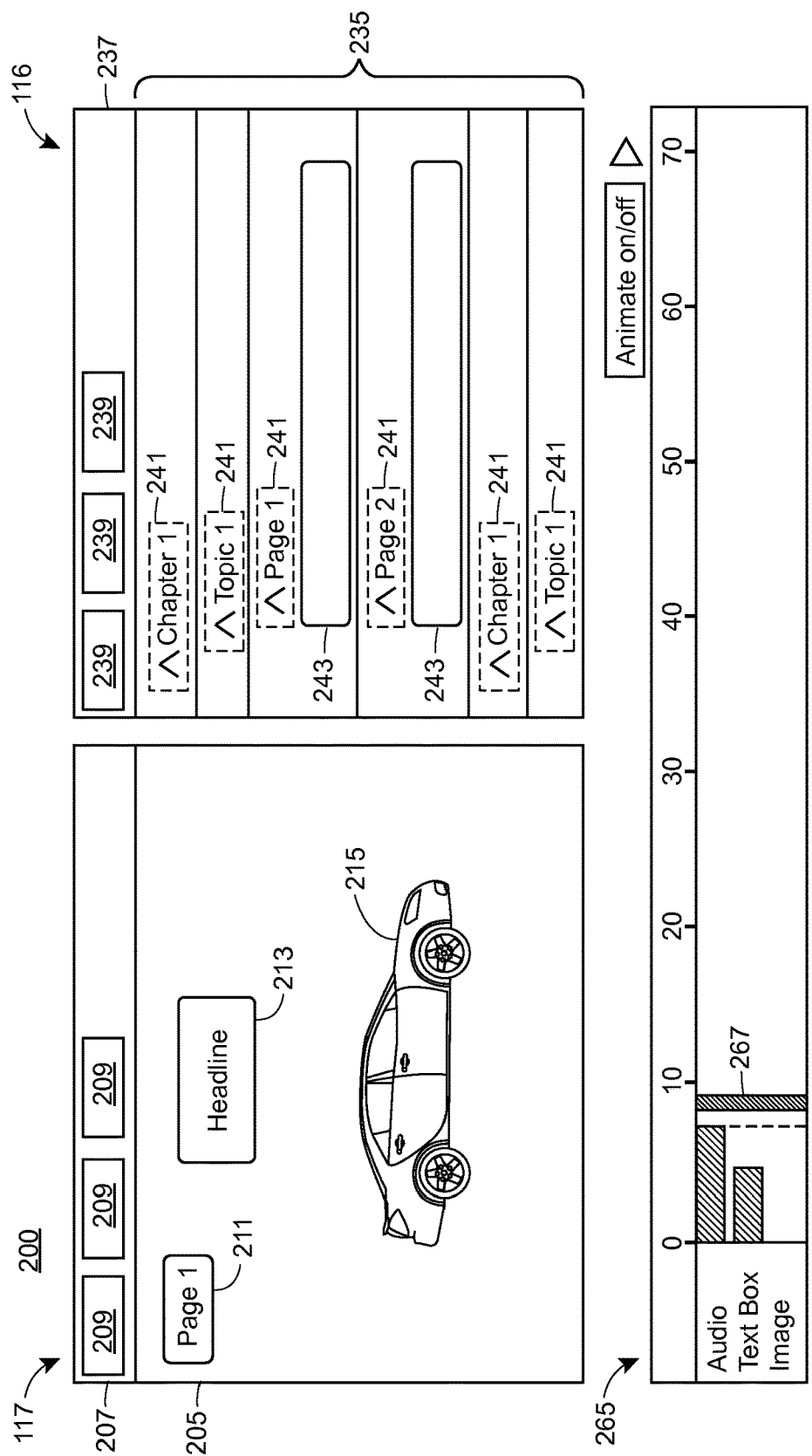
FIG. 2 depicts an example display that may be provided by a display device when the audio interface and the visual interface are displayed, according to an embodiment.

FIG. 2 depicts an example display 200 that may be provided by a display device when the audio interface 116 and the visual interface 117 are displayed, according to an embodiment. While FIG. 2 depicts the audio interface 116 and visual interface 117 displayed simultaneously, it will be appreciated that in some embodiments the audio interface 116 and visual interface 117 may be displayed independently of each other.

1. Audio Interface 116

In an embodiment, the audio interface 116 may include a design area 235 and/or a toolbar 237. The design area 235 may list one or more nodes 126 (shown in FIG. 1B) included in the IMP 125 (shown in FIG. 1B). The listed nodes 126 may be identified by a node identifier 241. In an embodiment, the designer may interact with a node identifier 241 to collapse the list of nodes within the particular node represented by that node identifier 241. For example, a designer may click on the node identifier 241 "Chapter 1" to collapse the nodes underneath it (i.e., "Topic 1," "Page 1," and "Page 2") so that the next node listed after "Chapter 1" is "Chapter 2." In some instances, the node identifiers 241 may include a graphic element to indicate whether or not the list of nodes within the identified node have been collapsed.

For each page listed in the design area 235, the audio interface 116 may include a text entry box 243. The designer may provide text in the text entry box 243 (e.g., via a physical or virtual keyboard) to define audio that will be presented when the associated page is presented at run-time for the IMP 125. For example, the designer may enter text in the text entry box 243 under the node identifier 241 labeled "Page 1" to define the audio that will be presented when "Page 1" of the IMP 125 is presented. The text may be converted to audio using a text-to-speech tool. In some instances, the audio is generated from the text via a recording of a human reading the text. Note, in some instances the audio interface 116 does not include a text entry box 243 for every page listed in the design area 235.

The toolbar 237 may include one or more input elements 239. Generally speaking, the input elements 239 are graphic elements that a designer may interact with (e.g., via a mouse click) to cause the IMP Authoring Tool 115 to perform a particular function. For example, in an embodiment a designer may interact with one of the input elements 239 to add an additional node to the listing within the design area 235. As a further example, a designer may interact with one or more of the input elements 239 to cut, copy, and/or paste nodes and/or text listed within the design area 235.

2. Visual Interface 117

In an embodiment, the visual interface 117 may include a design area 205 and/or a toolbar 207. Generally, the design area 205 enables a designer to select visual content assets to be displayed when a particular page of the IMP 125 is displayed. In particular, the design area 205 enables the designer to select a visual content asset by placing the visual content asset (or icon representing the visual content asset) in the design area 205. The visual interface 117 may include a page identifier 211 identifying the page of the IMP 125 that is being edited.

Examples of visual content assets include images, videos, or text. For example, the design area 205 includes a text box 213 specifying text to be presented when a page is presented, as well as an image 215 to be presented when a page is presented. In some instances, a designer may define an animation to be presented with a page. The designer may utilize the timeline 265 to define animations. In particular, the designer may specify particular locations on the page for the visual content assets at a first point in time. The designer may specify other locations on the page for the visual content assets at a second point in time, at a third point in time, etc. By defining locations of the content assets for particular points in time, the designer can define animation for the content assets. In an embodiment, the designer may drag a time marker 267 to a particular point of the timeline 265. The designer may position visual content assets within the design area 205 to define page locations for the visual contents at that particular point in time. In some embodiments, the timeline 265 may include a "play button," enabling a designer to preview animation.

The toolbar 207 may include one or more input elements 209, which may be similar in nature to the input elements 239. For example, in an embodiment a designer may interact with one of the input elements 209 to add a visual content asset to the design area 205. To illustrate, clicking on one of the input elements 209 may cause the IMP Authoring Tool 115 to display a library of visual content assets that may be selected and/or "dragged" to the design area 205. As a further example, a designer may interact with one or more of the input elements 239 to cut, copy, and/or paste visual content assets within the design area 235.

B. Display 300 of the Flow Interface 118

Figure 3:
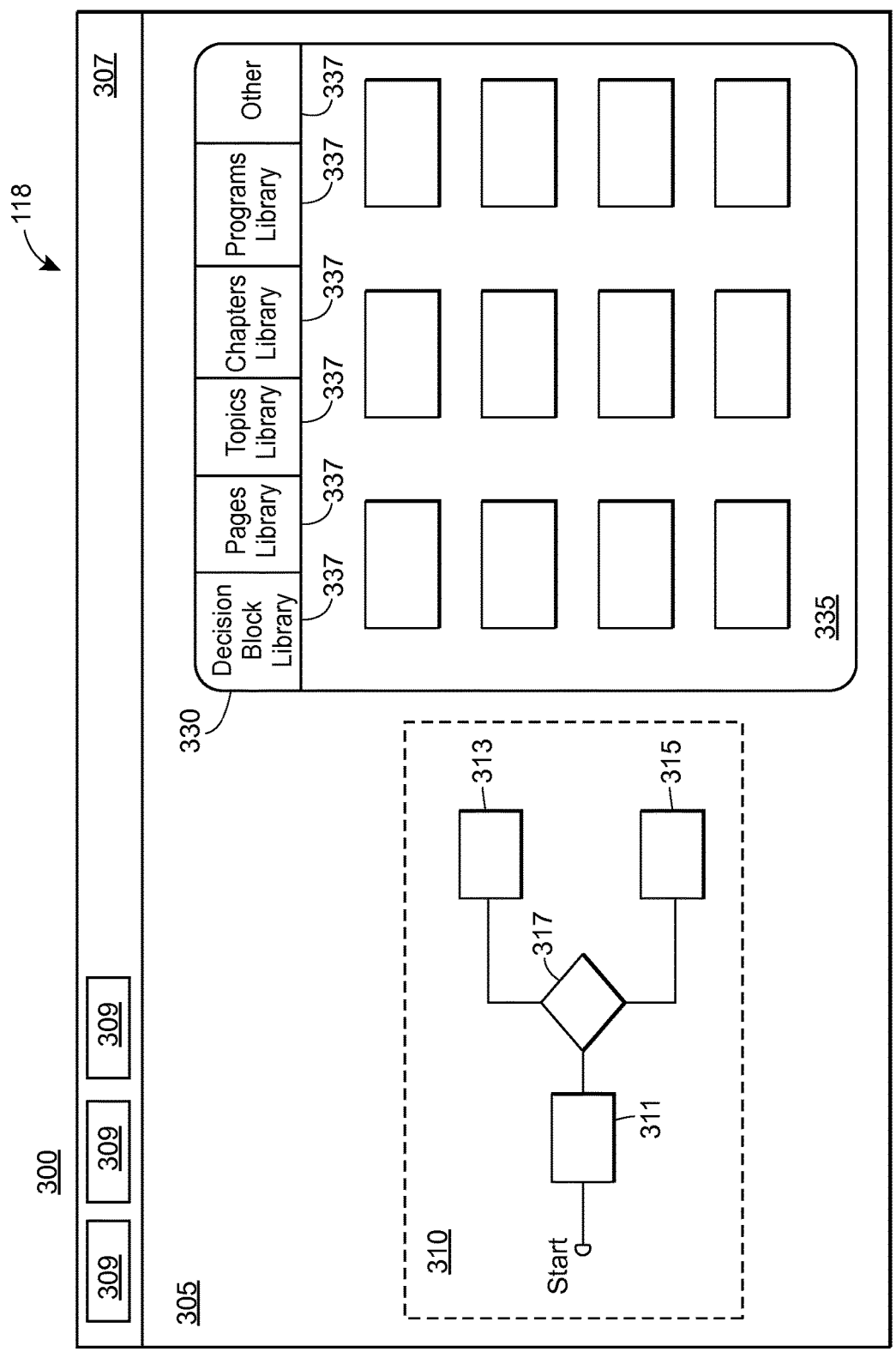
FIG. 3 depicts an example display that may be provided by a display device when a flow interface is displayed, according to an embodiment.

FIG. 3 depicts an example display 300 that may be provided by a display device when the flow interface 118 is displayed, according to an embodiment. It will be appreciated that in some embodiments the flow interface 118 may be displayed simultaneously with the audio interface 116 or the visual interface 117. In some embodiments, the audio interface 116, visual interface 117, and flow interface 118 may all be displayed at the same time via a single display device or group of display devices.

In an embodiment, the flow interface 118 may include a design area 305 and/or a toolbar 307. As depicted, the design area 305 includes a flow-definition 310 and a library 330.

Generally speaking, a designer may specify nodes 126 to be included in the IMP 125 by placing "blocks" (i.e., graphical representations of the specified nodes 126) in the design area 305. The designer may then connect the blocks to establish a block tree or flow-definition 310 for the IMP 125. In some instances a flow-definition 310 may include a single block. In other instances, a flow-definition 310 may include multiple blocks. In short, the flow-definition 310 defines nodes 126 to be potentially activated during runtime of the IMP 125, as well as a potential order for activating the nodes 126. More particularly, the IMP Authoring Tool 115 (shown in FIG. 1B) may populate the knowledge base 140 (shown in FIG. 1B) with rules 130 and/or facts 135 according to the flow-definition 310 specified by the designer. During run-time of the IMP 125, the rules engine 128 may identify the next node or nodes 126 to activate by evaluating, during run-time, the rules 130 and/or facts 135 in the knowledge base 140. The identified node or nodes 126 may be communicated to the content provision unit 129 (shown in FIG. 1B), and the content provision unit 129 may transmit the content associated with the next node or nodes 126 to the IMP Player 120.

It will be appreciated that, depending on the particular flow-definition 310 for an IMP 125, the IMP 125 may not necessarily activate every node 126 represented by the blocks placed in the design area 305. For example, the depicted flow-definition 310 includes blocks 311-317. Because block 317 is a decision block, the IMP 125 (as defined in this particular example) may not activate both nodes represented by blocks 313 and 315. Rather, for this particular example, during execution of the IMP 125, the rules engine 128 (shown in FIG. 1) may evaluate the rules and facts in the knowledge base 140 (populated, as noted, based on the flow-definition 310) to determine which of the nodes corresponding to the blocks 313 and 315 to activate.

While the exact determination regarding node-selection and order of presentation may not be known until run-time (because node-selection and order of presentation may depend on conditions and facts that are not evaluated until run-time), the flow defines a broad structure or outline for presentation of the IMP 125.

The library 330 includes tabs 337 and stencils 335. The stencils 335 essentially represent pre-configured nodes. For example, a stencil may represent a page or program that has already been designed or configured to a certain extent. Some stencils 335 may require further configuration. Other stencils 335 may not require further configuration. A designer may add blocks to the design area 305 by dragging stencils 335 from the library 330 and dropping them onto the design area 305. The tabs 337 may specify categories or types of stencil 335.

C. Display 400 of the Flow Interface 118

Figure 4:
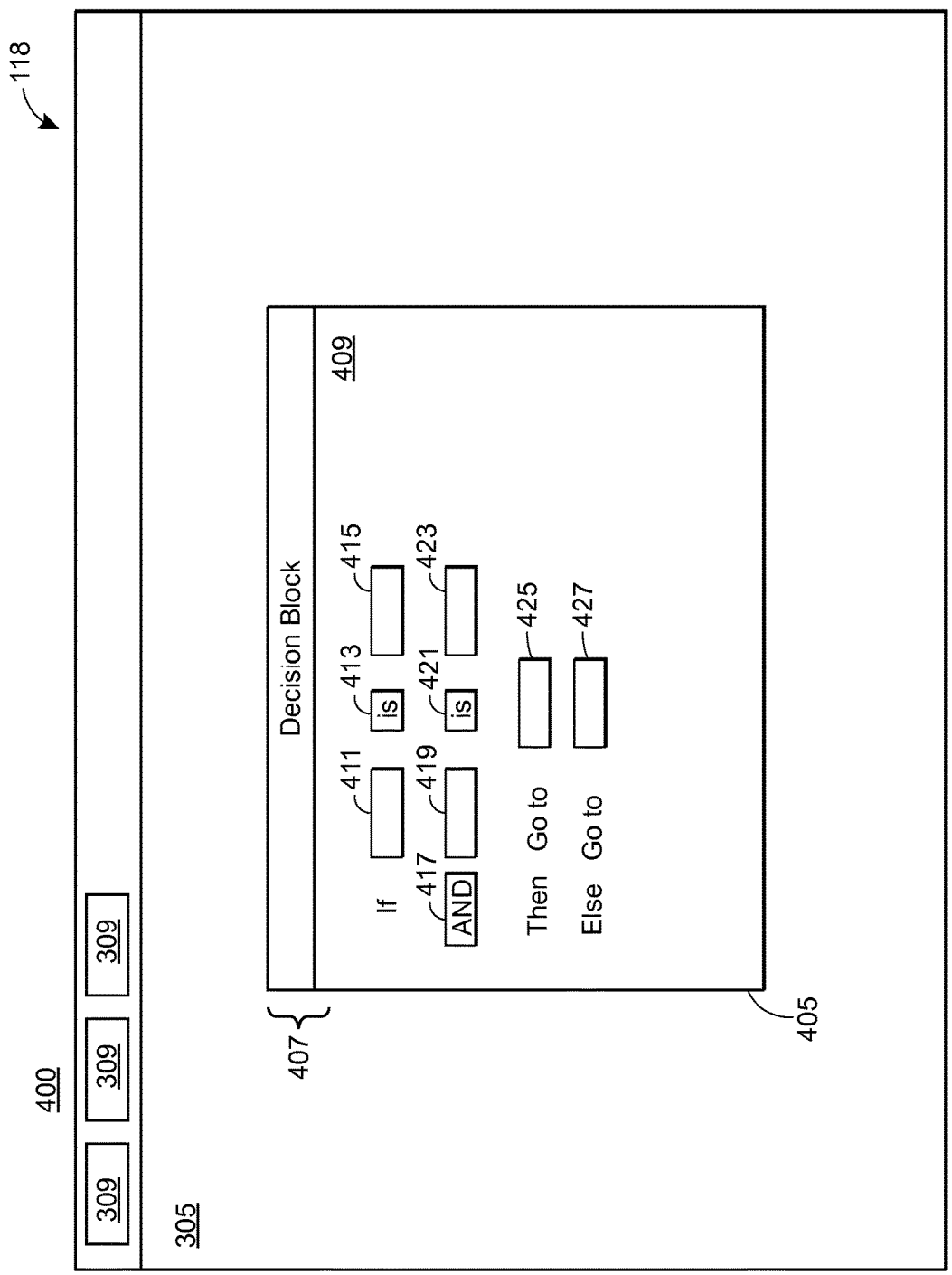
FIG. 4 depicts an example display that may be provided by a display device when a flow interface is displayed, according to an embodiment.

FIG. 4 depicts an example display 400 that may be provided by a display device when the flow interface 118 is displayed, according to an embodiment. In particular, FIG. 4 depicts an editor 405 for a decision block (such as the decision block 317 shown in FIG. 3). The editor 405 may be activated by a designer interacting with a decision block (e.g., click on the decision block) depicted in the design area 305 of the flow interface 118.

The editor includes a title bar 407 and a decision definition area 409. A designer may use the decision definition area 409 to define the logic to be used for selecting a next node to activate after a decision block. To illustrate, the editor 405 includes a variable elements 411 and 419; operator elements 413, 417, and 421; and value elements 415 and 423. The designer may interact with this elements to define a logical expression. Further, the designer may specify next nodes to activate, depending on the evaluation of the logical expression, using the node elements 425 and 427.

D. Display 500 of the Flow Interface 118

Figure 5:
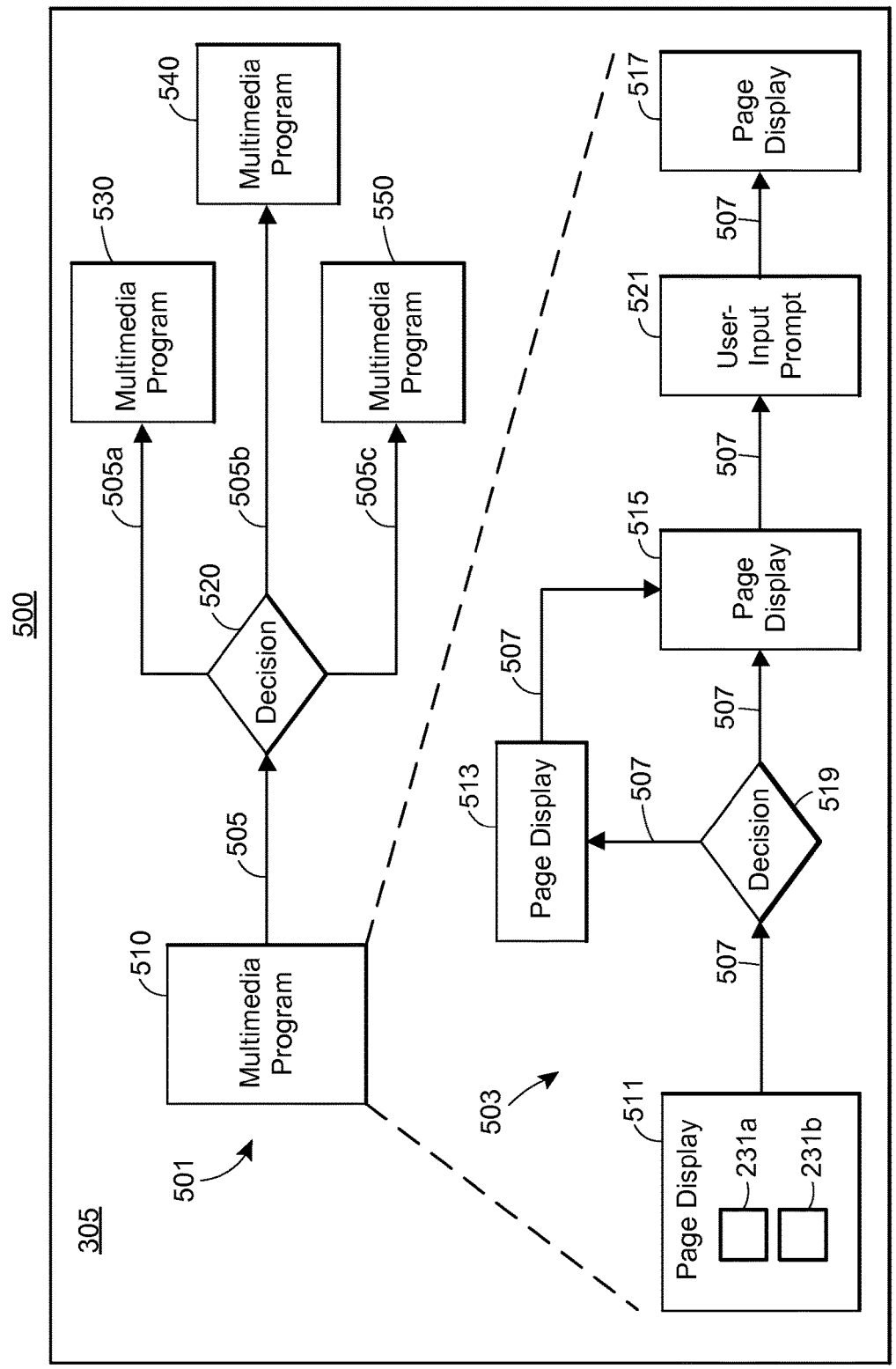
FIG. 5 depicts an example display that may be provided by a display device when a design area of the flow interface is displayed, according to an embodiment.

FIG. 5 depicts an example display 500 that may be provided by a display device when the design area 305 (shown in FIG. 3) of the flow interface 118 is displayed, according to an embodiment.

As shown, the design area 305 includes a block tree or flow-definition 501 and a block tree or flow-definition 503. The flow-definition 501 is defined according to the blocks 510-550 and links 505 connecting the blocks 210-250. Similarly, the flow-definition 503 is defined according to the blocks 511-519 and the links 505 connecting the blocks 511-519.

The blocks 510-550 are program blocks, each of which represents a collection of blocks having a particular flow-definition. For example, the program 510 includes the blocks 511-519 and links 507 defining the flow-definition 503. A designer may bind or associate a fact with the decision block 520 (using, e.g., the editor 405 shown in FIG. 4). For example, a designer may bind an age variable with the decision block 520, where the links 505a-d correspond to the potential values for the age variable. For example, link 505a may correspond to a value of 0-29; link 505b may correspond to a value of 30-60; and link 505c may correspond to a value of 60-120. In other words, the program that is activated during IMP presentation may depend on the facts in the knowledge base.

The flow-definition 503 includes output blocks 511-517, a decision block 519, and an input-prompt block 521. Each of the output blocks 511-517 may correspond to a node 126 that presents via the IMP Player 120 a page display ("page") when activated. In other words, a designer may create an output block 511 to design a page that is displayed when the corresponding node 126 is executed. The designer may design the page by selecting one or more multimedia content assets to be presented with the page (e.g., identifying the assets by file name). The node 126 corresponding to the created output block defining the page may present the selected content asset (via the IMP Player 120) if and when activated during IMP presentation.

The input-prompt block (sometimes referred to as a rule block or rule definition block, as it is generally used to define a rule) 521 may be used to design an input-prompt graphic (e.g., asking the user to answer a question) that is presented when a node 126 corresponding to the input-prompt block 521 is activated. The designer may specify the prompt and/or variables (i.e., facts) that may be defined based on the end-user's answer. Because the block 521 may be used to generate or define a new fact, it may be understood as a rule (which may be stored in the knowledge base) for obtaining a new fact.

For example, the designer may specify text for the input-prompt block 521 such as "What is your blood type?" The designer may further specify text to be associated with radio buttons so that an end-user may answer the question (e.g., "A−," "O+," etc.). When a node 126 presents the input-prompt corresponding to the input-prompt block 521, the received answer may be inserted into the knowledge base 140 as a new fact.

V. Example IMP Authoring System

Figure 6:
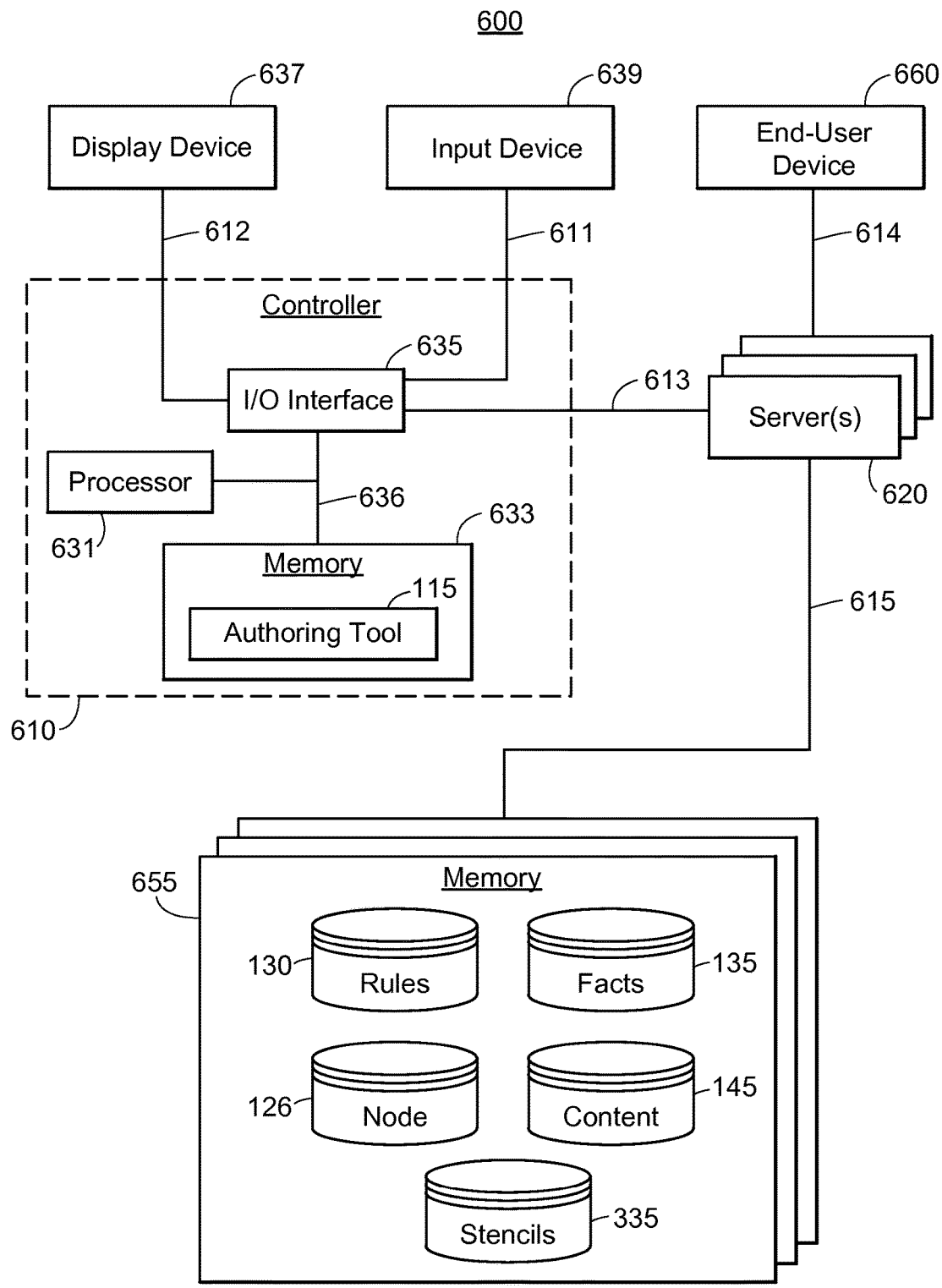
FIG. 6 depicts a block diagram of an example IMP Authoring System according to an embodiment.

FIG. 6 depicts a block diagram of an example IMP Authoring System 600 according to an embodiment. The IMP Authoring System 600 may include a controller 610, one or more display devices 637 (e.g., a screen or a monitor), one or more input devices 639 (e.g., touchscreen sensors, a mouse, keyboard, etc.), one or more servers 620, and one or more memory devices 655.

A. Example Structure Associated with the Controller 610

The controller 610 may be communicatively connected to the input device 639 via the link 611, and may be communicatively connected to the display device 637 via the link 612. In an embodiment, the link 611 is wired in nature (e.g., a USB cable). In an embodiment, the link 611 is wireless in nature (e.g., a Bluetooth™ link). Similar to the link 611, the link 612 may be wired or wireless in nature depending on the embodiment. The controller 610 may be communicatively connected to the one or more servers 620 via the link 613. The link 613 may include one or more intermediary devices and links, some of which may be part of a network such as the network 110 shown in FIG. 1B.

The controller 610 may include a processor 631, a memory device 633, and/or an I/O interface 635, each of which may be communicatively connected via a link 636. In an embodiment, the controller 610 includes multiple processors 631. In an embodiment, the link 636 is a system bus.

The memory 633 may store the IMP Authoring Tool 115 (described with reference to FIG. 1B). The memory 633 may include one or more memory devices including computer-readable media, and may include volatile and/or non-volatile memory.

The I/O interface 635 may include one or more interfaces for sending and receiving data and/or instructions, such as a video interface, an input-interface, a communication-interface etc. The I/O interface 635 enables the controller 610 to establish a connection to other networks, systems, and/or devices. The I/O interface 635 may include a wireless interface (e.g., for establishing an RF connection, such as a Bluetooth™ connection) and/or a wired interface (e.g., for establishing connection via an Ethernet cable or USB cable).

In some embodiments, the functionality of the IMP Authoring System 600 is provided entirely by the controller 610. In such embodiments, the IMP Authoring System 600 may not include any of the servers 620.

B. Example Structure Associated with the Server(s) 620

The one or more servers 620 may be communicatively connected to an end-user or client device 660 via a link 614, and may be communicatively connected to the one or more memory devices 655 via a link 615. Each of the links 614 and 615 may include one or more intermediary devices and links, some of which may be part of a network such as the network 110 shown in FIG. 1B.

The memory device(s) 655 may store data representing rules 130, facts 135, nodes 126, content 145, and/or stencils 335. In an embodiment, the data in the knowledge base 140 shown in FIG. 1B is stored at one or more of the memory devices 655.

In some embodiments, the data representing one or more of the rules 130, facts 135, nodes 126, content 145, and/or stencils 335 may be stored at the memory device 633 of the controller 610.

C. Example Operation Associated with the IMP Authoring System 600

In example operation, the processor 631 executes a set of instructions or routines representing the IMP Authoring Tool 115 to cause the controller 610 to provide a GUI (e.g., via the display device 637) for designing or creating an IMP 125. The provided GUI may include one or more of the audio interface 116, the visual interface 117, or the flow interface 118 shown in FIG. 1B.

The controller 610 may cause the display device 637 to display the audio interface 116 shown in FIG. 1B to enable a designer to edit audio for a particular page in the IMP 125 (shown in FIG. 1B). The controller 610 may receive input data from the one or more input devices 639. For example, the controller 610 may receive text-data from a keyboard. The controller 610 may utilize a text-to-speech tool (stored, e.g., at the memory device 633 or at the memory device 655) to convert the text-data to audio data. The audio data may then be stored to memory (e.g., as content data 145), and the controller 610 may store to memory page data (e.g., node data 126) for the edited page so that the page data references the audio data. Consequently, when the IMP 125 is later presented at the client device 660 and the edited page needs to be presented, one of the servers 620 (e.g., which may be implementing the rules engine 128 and/or the content provision unit 129 shown in FIG. 1B) may reference the node data 126 to determine which audio file or data in the content database 145 should be transmitted to the client device 660 for presentation.

The controller 610 may cause the display device 637 to display the visual interface 117 shown in FIG. 1B to enable a designer to edit visual(s) for a particular page in the IMP 125. The controller 610 may receive input data from the one or more input devices 639. For example, the controller 610 may receive input-data from a mouse as the designer selects images from a library or file directory to be placed on the design area 205. Further, the controller 610 may receive text-data from a keyboard as a designer defines text to be displayed on the particular page. If the defined visuals are not already stored at the memory device(s) 655, the controller 610 may communicate with the servers 620 to store the visual data at the memory device(s) 655 as content data 145. The controller 610 may store to memory (e.g., at the memory device 655) page data (e.g., node data 126) for the edited page so that the page data references the defined visuals represented by the visual data. Consequently, when the IMP 125 is later presented at the client device 660 and the edited page needs to be presented, one of the servers 620 (e.g., which may be implementing the rules engine 128 or the content provision unit 129) can reference the node data 126 to determine which file or data in the content database 145 should be transmitted to the client device 660 for presentation.

The controller 610 may cause the display device 637 to display the flow interface 118 shown in FIG. 1B to enable a designer to define a flow between nodes of the IMP 125. The controller 610 may receive input data from the one or more input devices 639. For example, the controller 610 may receive input-data from a mouse as the designer drags and drops stencils 335 onto the design area 305 shown in FIG. 3 and defines a flow by connecting the created blocks. The controller 610 may then communicate with the server(s) 620 to store at the memory device data representing rules 130 and/or facts 135 generated based on the flow-definition created in the design area 305. In other words, the controller 610 may populate the knowledge base 140 based on the provided flow definition. Consequently, when the IMP 125 is later presented at the client device 660, one of the servers 620 can reference the rules 130 and/or facts 135 to determine a next node or nodes for presentation. In other words, the server 620 can references the rules 130 and/or facts 135 to determine, in or near real-time, nodes to be presented and an order for presenting the nodes.

Note, each stencil 335 may represent a template block. For example, the stencils 335 may include input-prompt stencils (e.g., a multiple-choice radio button input prompts), output stencils (e.g., page displays having a particular layout for presenting multimedia content), collection-node stencils (e.g., representing a program, edition, chapter, sequence, etc.), and/or decision stencils. Once a stencil 335 has been placed in the design area to create a new block, the designer may specify particular attributes or attribute values for the new block. For example, the designer may specify particular multimedia content to be presented (e.g., via a filename), specify particular questions to ask the end-user, etc.

It will be understood that in some embodiments, one or more of the various links connecting components of the IMP Authoring System 600 (i.e., links 611-615 and link 636) may include intermediary links or devices not shown in FIG. 6. For example, the link 613 between the controller 610 and the server(s) 620 may include intermediary routers, modems, switches, and other networking devices, as well as all of the communicative links between each of those intermediary devices. Further, each of the displayed links may include intermediary wireless links and/or intermediary wired links, depending on the embodiment.

VI. Example Method for Authoring an IMP

Figure 7:
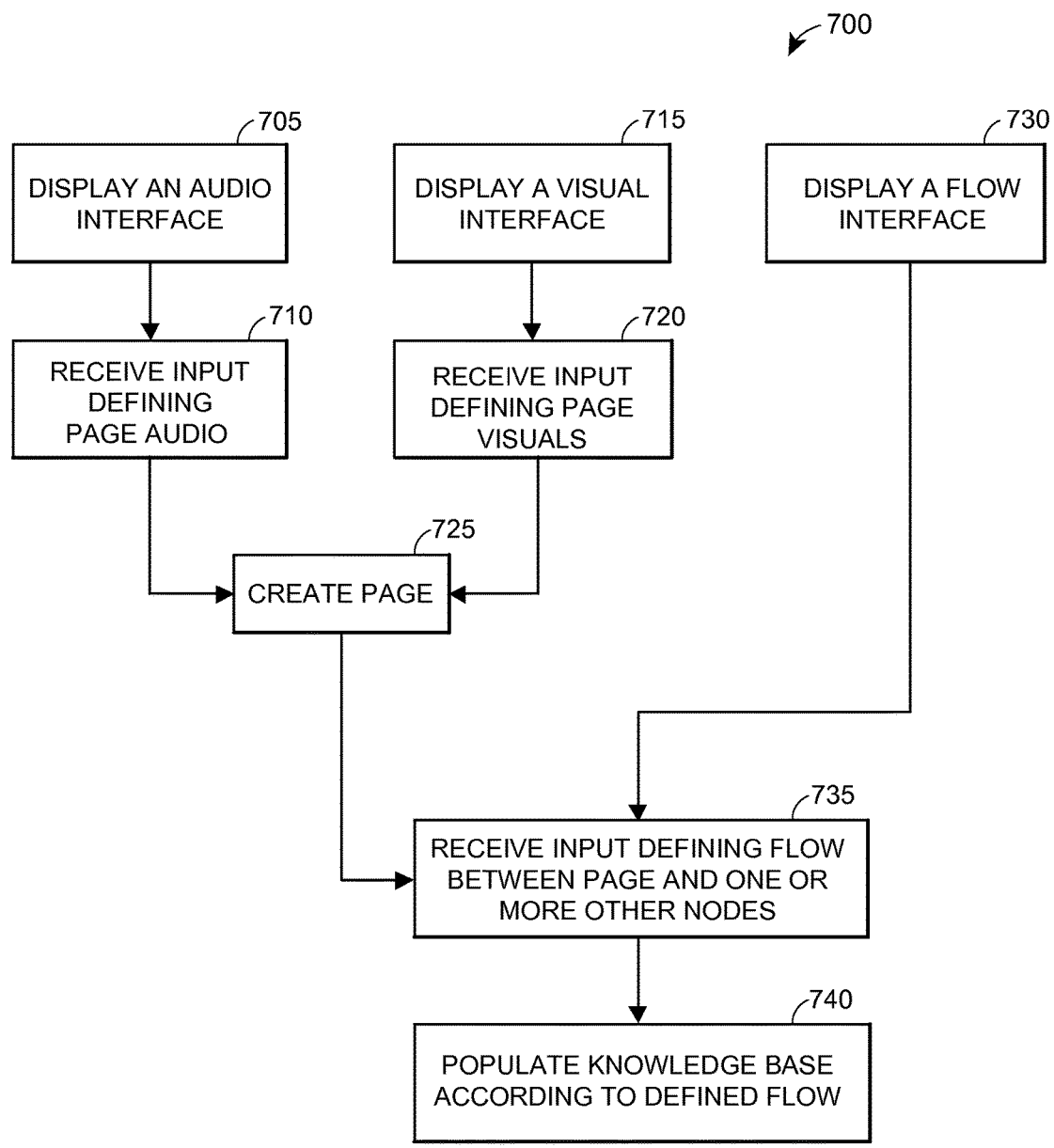
FIG. 7 depicts an example method for authoring an IMP according to an embodiment.

FIG. 7 depicts an example method 700 for authoring an IMP. The method 700 may be implemented, in whole or in part, on one or more devices or systems such as those shown in the system 100 of FIG. 1B and IMP Authoring System 600 of FIG. 6. In particular, the method 700 may be implemented by the IMP Authoring Tool 115 shown in FIG. 1B and/or the controller 610 shown in FIG. 6. The method may be saved as a set of instructions, routines, programs, or modules on memory, such as the memory device 633 or the memory device 655 shown in FIG. 6.

Method 700 begins when the audio interface 116, visual interface 117, or flow interface 118 (blocks 705, 715, 730) is displayed. The interfaces may be displayed via the display device 637 shown in FIG. 6. In an embodiment, the interfaces 116-118 may be presented in any order. In an embodiment, all three interfaces 116-118 are presented simultaneously. Further, all three interfaces 116-118 may be presented via a single display.

The controller 610 may receive input data defining an audio content asset to be presented with a particular page of the IMP 125 (block 710). The input data may be keystroke data received from a keyboard used by a designer to type text in a text entry box 243 (shown in FIG. 2) included in the audio interface 116 displayed at the display device 637. In an embodiment, the input data may be audio data received from a microphone used by a designer to vocalize the audio represented by the audio content asset.

The controller 610 may receive input data defining a visual content asset to be presented with the particular page of the IMP 125 (block 720). The input data may be keystroke data received from a keyboard (which may be physical or virtual), mouse data received from a mouse, touchscreen data received from a touchscreen, or some other data received from another input device used to select a visual (such as an image) to be placed with in the design area 205 (shown in FIG. 2) included in the visual interface 117 displayed at the display device 637.

The controller 610 may create a page by storing to memory (e.g., memory device 655 or memory device 633) page data representing the created page (block 725). The page data may reference audio and visual content assets selected or defined via the input data received at the controller 610.

The controller 610 may receive input data defining a flow between the created page and one or more other nodes of the IMP 125 (block 735).

The controller 610 may populate the knowledge base 140 (shown in FIG. 1B) with rules 130 and/or facts 135 according to the flow-definition created via the flow interface 118 (block 740).

VII. Example IMP Player System

Figure 8:
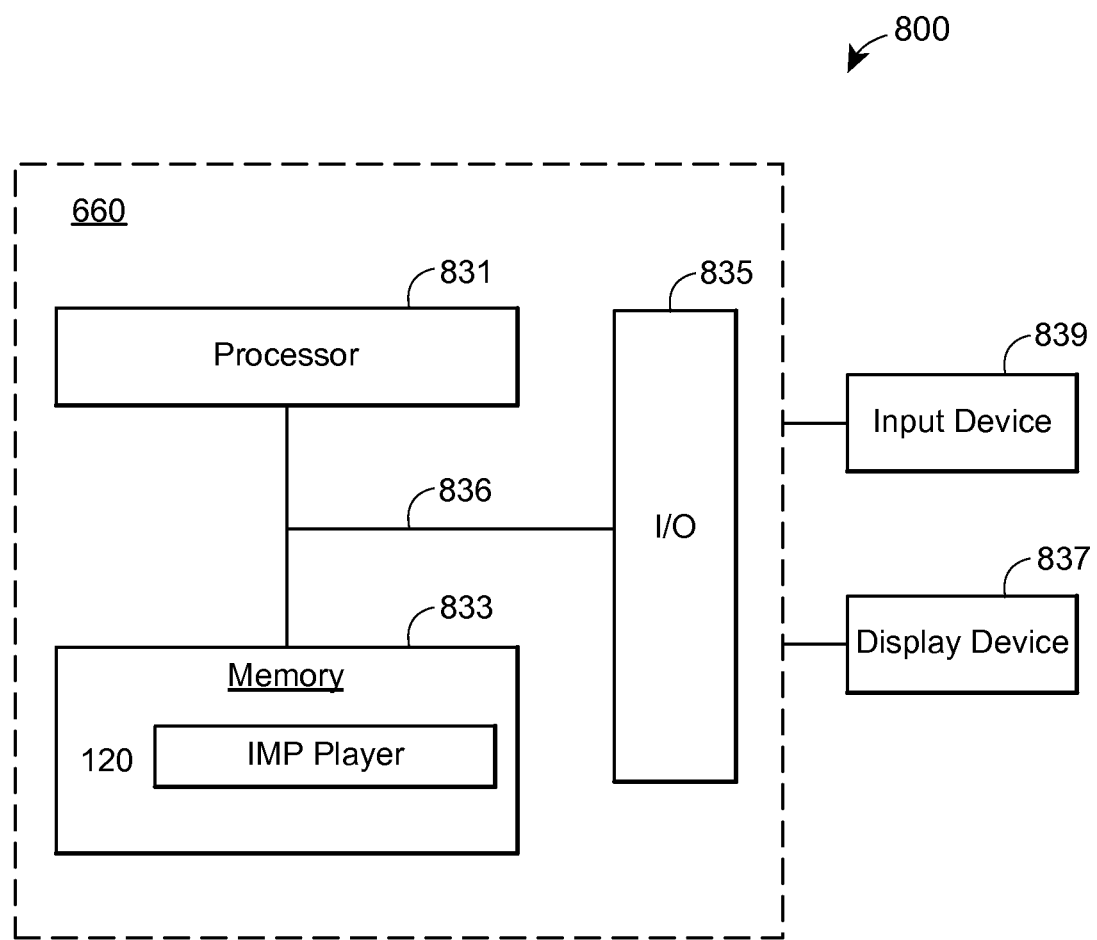
FIG. 8 depicts a block diagram of an example IMP Player System according to an embodiment.

FIG. 8 depicts a block diagram of an example IMP Player System 800, according to an embodiment. The IMP Player System 800 may be utilized to present one or more IMPs 125 (shown in FIG. 1B).

A. Example Structure Associated with the IMP Player System 800

In an embodiment, the IMP Player System 800 includes the end-user device 660 of FIG. 6 (also referred to herein as client device 660). Generally speaking, the client device 660 is an electronic device capable of presenting audio and/or visual content. For example, the client device 660 may be a desktop computer, a laptop computer, a tablet, a mobile phone, a set-top box (e.g., for providing audio/video to a television), a personal digital assistant, a wearable device (e.g., a smart watch), etc. Regardless of its precise form, the client device 660 may present one or more IMPs 125. Presenting an IMP 125, or a part of an IMP 125, may include presenting one or more content assets. For example, the client device 660 may display one or more visual content assets and/or may audibly produce one or more audio content assets.

In an embodiment, the client device 660 may include, or be coupled to, an input device 839 (e.g., touchscreen sensors, a mouse, keyboard, etc.) and/or a display device 837 (e.g., a screen or a monitor). In an embodiment, the client device 660 includes a processor 831, which may be coupled to a memory 833 and an I/O interface 835 via a bus 836.

The I/O interface 835 may include one or more interfaces for sending and receiving data and/or instructions, such as a communication interface, a video interface, an input-interface, etc. Further, in some embodiments the controller 810 includes multiple processors 831. The client device 660 may utilize the I/O interface 835 to connect to the network 110 shown in FIG. 1B, enabling the client device 660 to establish connection with the rules engine 128 and/or the content provision unit 129. Further, the client device 660 may utilize the I/O interface 835 to connect to the servers 620 via the link 614 shown in FIG. 6.

The memory 833 may store instructions or routines representing the IMP Player 120 (described with reference to FIG. 1B). The memory 833 may include one or more memory devices including computer-readable media, and may include volatile and/or non-volatile memory such as read-only memory (ROM) and/or random access memory (RAM), for example. In an embodiment, the memory 833 includes a program storage storing programs/instructions that may be executed by the processor(s) 831, and a data storage storing data used by those programs when executed by the processor(s) 831. The programs stored in program storage may include a web browser application. When executed by processor(s) 831, the web browser application may provide an HTML5-capable web browser, for example. In an embodiment, the memory 833 includes data for presenting at least part of an IMP 125. This data may be received by the client device 660 from one or more of the servers 620 shown in FIG. 6. As an example, the memory 833 may include one or more visual content assets and/or one or more audio content assets that, for example, were previously stored at the content database 145.

In an embodiment, the client device 660 may include, or be coupled to, an audio device (e.g., a speaker). Such an audio device may be coupled to the I/O interface 835.

B. Example Operation Associated with the IMP Player System 800

In example operation, the IMP Player System 800 may present an IMP 125. For example, the processor 831 may execute a set of instructions or routines representing the IMP Player 120 to cause the client device 660 to provide a GUI (e.g., via the display device 837) for presenting an IMP 125, in accordance with the rules 130 as implemented by the rules engine 128 (as described above). The GUI may be provided based on data received via the I/O interface 835. For example, the GUI may include one or more visual content assets of an IMP presentation. In an embodiment, executing the instructions representing the IMP Player 120 may cause the client device 660 to produce audio (e.g., via an audio device coupled to the client device 660) for presenting the IMP 125. Thus, the client device 660 may present one or more audio content assets of the IMP 125.

C. Example Presentation 900

Figure 9:
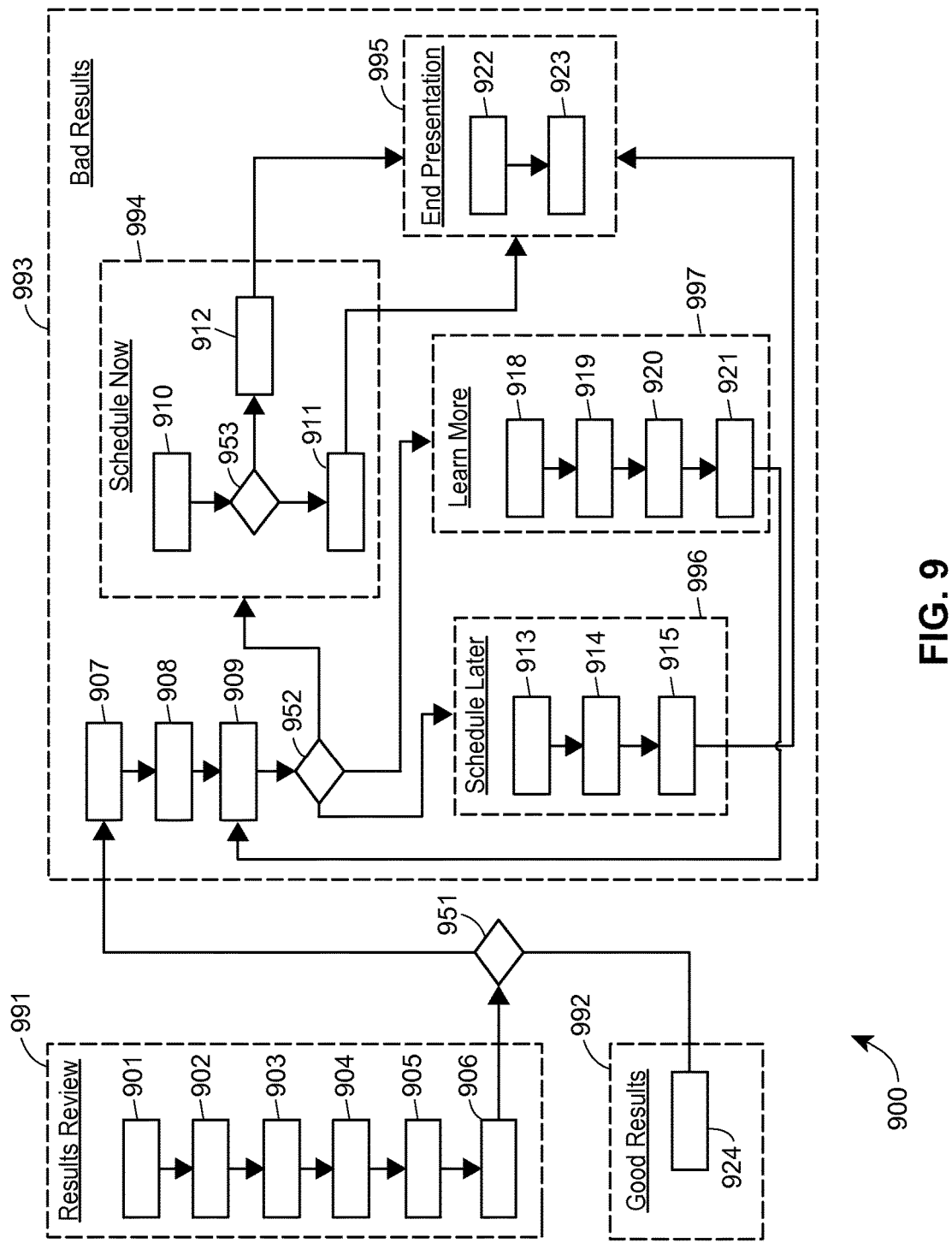
FIG. 9 depicts an example presentation of an IMP according to an embodiment.

To further illustrate, FIG. 9 depicts an example presentation 900 of an IMP according to an embodiment. Pages of the presentation 900 may be presented by way of the client device 660 (e.g., by way of the display device 837 and/or by way of an audio device coupled to the client device 660). The presentation 900 may be facilitated, in whole or in part, by rules engine 128, content provision unit 129, and/or one or more of the servers 620. The presentation 900 includes various collections of pages. Generally speaking, these collections may be understood as corresponding to the previously described collection-nodes. The pages of each collection may be understood as pertaining to a similar goal or function.

For example, the pages of collection 991 may be implemented to facilitate reviewing results of a test with a user. After the collection 991 is presented, the page(s) of collection 992 may be presented when the user's test results are good, and the pages of collection 993 may be presented when the user's test results are bad. The pages of collection 994 may be presented when a user wants to schedule an appointment in real-time. The pages of collection 995 may be presented to end a presentation. The pages of collection 996 may be presented when a user wants to schedule an appointment at a later time. The pages of collection 997 may be presented when a user wants to learn more about a particular topic.

1. Collection 991: Review of Results

The client device 660 may receive data representing at least part of an IMP 125. The data may be received via the I/O interface 635 (e.g., via a network interface) of the client device 660.

Based on the received data, the client device 660 may present a page 901 of the IMP 125 including the message: "Hi! It's nice to see you." The page 901 may be presented by displaying text of the message and/or producing audio of the message. Similarly, the messages of some or all of the pages described below may be presented by displaying text and/or producing audio of the respective message.

The client device 660 may present a page 902 including the message: "Today I'd like to go over your latest A1C results together." The A1C test is a blood test used to diagnose diabetes and to gauge how well a patent is managing diabetes.

The client device 660 may present a page 903 including the message: "As you know, your A1C tells how well your blood sugar was controlled over the past 3 months. Let's take a look." In an embodiment, one or more visual content assets may be provided along with the message. For example, an image of a calendar may be provided.

The client device 660 may present a page 904 including the message: "Here are the results of your last two A1C scores." One or more visual content assets representing the scores may be presented. Additionally or alternatively, one or more audio content assets representing the scores may be presented (e.g., the scores may be "read" to the user via an IVR system).

The client device 660 may present a page 905 including one of the following messages: (i) "Your doctor would like you A1C score to be 6.5 or less;" (ii) "Your doctor would like you A1C score to be 7 or less;" or (iii) "Your doctor would like you A1C score to be 8 or less." The decision of which message to present may depend on rules 130 and/or facts 135 in the knowledge base 140 (shown in FIG. 1B). For example, the selected message may depend on the user's actual score, which may be stored as a fact 135. The rules engine 128 (shown in FIG. 1B) may decide which message to present, and may send a signal to the client device 660 to notify the client device 660 which message is to be presented.

The client device 660 may present a page 906 including one of the following messages: (i) "Great job staying on track! You've really got a handle on this;" (ii) "Well done! You really turned it around;" (iii) "OK. Looks like you might need a little help. A check in can help get you moving in the right direction. So your health care team wants to see you for an appointment soon;" or (iv) "Keeping blood sugar under control can be TOUGH. Since both of your recent test results have been higher than your goal, your health care team wants to see you for an appointment soon." The decision of which of the four messages to present may depend on the one or more rules 130 and/or facts 135. For example, the decision may depend on the user's most recent score and his or her second most recent score. The user's scores may be graded as good or bad (e.g., based on predetermined thresholds stored at the knowledge base 140). If the user has two good scores, the first message may be presented. If the user had a bad score and then a good score, the second message may be presented. If the user had a good score and then a bad score, the third message may be presented. If the user had two bad scores, the fourth message may be presented.

2. Decision-Point 951: Analysis of Most Recent Score

If the user's most recent score was bad, the client device 660 may present a page 907. On the other hand, if the user's most recent score was good, the client device 660 may present a page 924. The analysis of the most recent score may be performed by the rules engine 128. The most recent score may be stored at one or more of the memory devices 655 shown in FIG. 6 and/or the knowledge base 140 shown in FIG. 1B (e.g., as a fact 135). In an embodiment, data for the pages of collection 992 or data for pages of collection 993 may be transmitted (e.g., by one or more of the servers 620) to the client device 660 based on the analysis. In an embodiment, the rules engine 128 may communicate with the content provision unit 129 to cause the content provision unit 129 to transfer audio and/or visual content assets to facilitate presentation of pages for the appropriate collection.

3. Collection 992: Follow-Up on Good Results

If the page 924 is displayed, it may include a message: "Now that you've got the ball rolling, this can be a great time to tackle any other struggles you might be having." The client device 660 may then present additional pages not displayed on FIG. 9. For example, the client device 660 may present a page with a prompt regarding other areas the user may be interested in, such as medication, exercise, nutrition, etc. The user might express interest in one of these areas (e.g., by clicking on an appropriate button or heading). The client device 660 might then present additional pages corresponding to the selected area. Eventually, the user may indicate that he or she is finished with the presentation (e.g., via a button or heading), causing the presentation to end.

4. Collection 993: Follow-Up on Bad Results

As noted, the client device 660 may present a page 907 if the user's A1C score was bad. The page 907 may include the following message: "You see, a high A1C means your blood sugar has been too high, which can cause health problems."

The client device 660 may present a page 908 including the following message: "The good news? Working together with your team, you can get control over your blood sugar and lower your A1C." The client device 660 may present one or more visual content assets to show members of the user's health care team. For example, in an embodiment, the client device 660 presents pictures of members of the health care team. In an embodiment, names of members of the health care team are shown.

The client device 660 may present a page 909 including the following message: "What do you think—should we get you scheduled for an appointment? Or would you like to learn more about A1C?"

a) Decision-Point 952: User Response

The client device 660 may receive from the user an answer to the question of page 909. For example, the user may verbalize his or her answer, and the client device 660 may receive the answer via a microphone (not shown in FIG. 8). As another example, the user may type his or her answer by way of a physical or virtual keyboard. As yet another example, the user may select from a number of options listed by the client device 660 (e.g., via the display device 837 shown in FIG. 8).

If the user responds to the message of page 909 by answering that she would like to schedule an appointment now, the client device 660 may present a page 910. If the user answers that she would like to learn more about A1C, the client device 660 may present a page 918. If the user answers that she would like to schedule an appointment later, the client device 660 may present a page 913.

b) Collection 994: Schedule Now

The page 910 may include the following message: "Great. I can call you now to connect you with someone at your doctor's office, or you can schedule online." The user may respond to this message by indicating that she would like to either speak on the phone or schedule an appointment online.

If the user responds to the message of page 910 by indicating that she would like to speak on the phone, the client device 660 may present a page 911 including the following message: "Got it. I'll call you in a minute to connect you with your doctor's office." The client device 660 may then communicate with one of the servers 620 to initiate a phone call or teleconference between the user and the doctor's office. The client device 660 may present a visual content asset to indicate to the user that a call is in the process of being placed (e.g., an image of a cell phone).

If the user responds to the message of page 910 by indicating that she would like to schedule online, the client device 660 may present a page 912 with the following message: "Got it. I'll take you to your doctor's online scheduling website." The client device 660 may activate a web browser (e.g., an application stored at the memory 833 shown in FIG. 8) and direct the browser to the appropriate website.

After presenting either the page 911 or the page 912, the client device 660 may end the presentation.

c) Collection 995: End Presentation

To end the presentation, the client device 660 may present a page 922 including the message: "Remember, by working together as a team, you have a better chance of gaining control over your health."

The client device 660 may present a page 923 including the message: "Thanks for watching. I wish you the best of health."

d) Collection 996: Schedule Later

Returning to the decision-point 952, if the user responds to the message of page 909 by indicating she would like to schedule an appointment later, the client device 660 may present a page 913 with the following message: "No problem. You can contact your doctor's office at this number." The client device 660 may present a visual content asset to provide the number to the user.

The client device 660 may present a page 914 with the following message: "How would you like me to send you this information?" The user may indicate (e.g., by interacting with a radio button) that her preferred method for receiving the information is, e.g., text, email, some other delivery channel, or some combination thereof.

After the user indicates her preferred method for receiving the information, the client device 660 may present a page 915 with the following message: "OK. I'll send that along in a minute."

After presenting the page 915, the client device 660 may end the presentation by presenting one or more of the pages in collection 995.

e) Collection 997: Learn More

Returning to page 909, if the user indicates that she would like to learn more, the client device 660 may present the page 918, which may include the following text: "The A1C is the blood sugar check your doctor needs to do every few months."

The client device 660 may present a page 919 including the message: "And controlling your blood sugar is the best way to avoid the serious problems diabetes can cause . . . even things like heart attacks and strokes."

The client device 660 may present a page 920 including the message: "But there's a lot you can do to control your blood sugar and prevent these problems."

The client device 660 may present a page 921 including the message: "In fact, your doctor or healthcare provider can help you with all of this."

After presenting the page 921, the client device 660 may end the presentation by presenting one or more of the pages in collection 995.

D. Additional, Alternative, or not Shown Aspects of the IMP Player System 800

In some embodiments, the IMP Player System 800 may include additional, fewer and/or different components than are shown in FIG. 8. Further, in some embodiments the IMP Player System 800 may include components arranged in a different manner than that shown in FIG. 8. In one embodiment, for example, the rules engine 128 may be stored and/or implemented at the client device 660. Moreover, in some embodiments, other functionality or data provided by the IMP Player System 800 may be provided by or at the client device 660 (e.g., the memory 833 may store the content database 145, the IMP database 125, and/or the knowledge base 140).

In some embodiments and/or scenarios, the client device 660 may be capable of receiving and presenting different IMP portions (e.g., programs) via one or more additional communication channels. For instance, the client device 660 may be a smartphone and, in addition to presenting IMP portions with multimedia content as described above, may include call capabilities allowing portions of the IMP to be presented to the end-user via IVR (interactive voice response), and/or texting capabilities allowing portions of the IMP to be presented to the end-user via SMS text messages. Alternatively, or additionally, the end-user may use one or more other devices, in addition to client device 660, to access different portions of the IMP. For instance, the client device 660 may be a tablet device, and the end-user may also have a landline phone via which IVR editions of various portions of the IMP may be presented to the end-user, and/or a mobile phone via which SMS text message editions (and/or IVR editions) of various potions of the IMP may be presented to the end-user.

VIII. Additional Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

A. Network(s)

As used herein, unless otherwise specified, the term "network" is a collection of nodes (e.g., devices or systems capable of sending, receiving and/or forwarding information) and links which are connected so as to enable telecommunication between the nodes.

Generally speaking, the term "node" (when used in reference to a network topology, and to be distinguished from the "nodes" discussed above in connection with FIGS. 1-8)

refers to a connection point, redistribution point, or a communication endpoint. A node may be any device or system (e.g., a computer system) capable of sending, receiving and/or forwarding information. For example, end systems that originate and/or ultimately receive a message are nodes. Intermediary device that receive and forward the message are also generally considered to be "nodes."

A "link" is a pathway or medium connecting two or more nodes. A link may be a physical link and/or a logical link. A physical link is the interface and/or medium(s) over which information is transferred, and may be wired or wireless in nature. Examples of physicals links may include a cable with a conductor for transmission of electrical energy, a fiber optic connection for transmission of light, and/or a wireless electromagnetic signal that carries information via changes made to one or more properties of an electromagnetic wave(s).

A logical link between two or more nodes represents an abstraction of the underlying physical links and/or intermediary nodes connecting the two or more nodes. For example, two or more nodes may be logically coupled via a logical link. The logical link may be established via any combination of physical links and intermediary nodes (e.g., routers, switches, or other networking equipment).

A link is sometimes referred to as communication channel. In a wireless communication system a channel generally refers to a particular frequency or frequency band. A carrier signal (or carrier wave) is transmitted at the particular frequency or within the particular frequency band of the channel. In some instances, multiple signals may be transmitted over a single band/channel. For example, signals may sometimes be simultaneously transmitted over a single band/channel via different sub-bands or sub-channels. As another example, signals may sometimes be transmitted via the same band by allocating time slots over which respective transmitters and receivers use the band in question.

As already noted, a network is a collection of nodes and links. A network may include dedicated routers responsible for directing traffic between nodes, and, optionally, dedicated devices responsible for configuring and managing the network. Some or all of the nodes may be also adapted to function as routers in order to direct traffic sent between other network devices. Network devices may be interconnected in a wired or wireless manner, and network devices may have different routing and transfer capabilities. For example, dedicated routers may be capable of high volume transmissions while some nodes may be capable of sending and receiving relatively little traffic over the same period of time. Additionally, the connections between nodes on a network may have different throughput capabilities and different attenuation characteristics. A fiberoptic cable, for example, may be capable of providing a bandwidth several orders of magnitude higher than a wireless link because of the difference in the inherent physical limitations of the medium. A network may include networks or subnetworks, such as a local area network (LAN) or a wide area network (WAN).

B. Communication Interface(s)

Some of the devices and/or systems described herein include a "communication interface" (sometimes referred to as a "network interface"). For example, the I/O interface 635 shown in FIG. 6 and the I/O interface 835 shown in FIG. 8 may each include a communication interface in some embodiments. A communication interface of a system enables the system (e.g., the controller 610 or client device 660) to send information to other system and/or receive information from other systems. In some instances, a communication interface of a system may be utilized to establish a direct connection to another system. In some instances, a communication interface of a system enables the system to connect to a network (via a link).

To illustrate, a communication interface can include circuitry for permitting wireless communication (e.g., short-range and/or long-range communication) with one or more devices or systems using any suitable communications protocol. For example, a communication interface may support Wi-Fi (e.g., an 802.11 protocol), Ethernet, Bluetooth™, high frequency systems (e.g., 900 MHZ, 2.4 GHZ, and 5.6 GHZ communication systems), infrared, transmission control protocol/internet protocol ("TCP/1P") (e. g., any of the protocols used in each of the TCP/IP layers), hypertext transfer protocol ("HTTP"), BitTorrent™, file transfer protocol ("FTP"), real-time transport protocol ("RTP"), real-time streaming protocol ("RTSP"), secure shell protocol ("SSH"), any other communications protocol, or any combination thereof. A communication interface of a system may also include circuitry that enables the system to be electrically or optically coupled to another device (e.g., via a coax cable or fiber optic cable) and communicate with that other device.

C. Hardware and Software System(s)/Module(s)

Additionally, certain embodiments are described herein as including logic or a number of routines, subroutines, applications, or instructions. These may constitute either software (e.g., code embodied on a machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules/systems/subsystems of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

D. Processor(s)

The various operations of example methods described herein may be performed, at least partially, by one or more processors. Such processors may be configured to fetch and execute instructions stored to memory. By executing these instructions, the processor can carry out various operations or functions.

The processors may be temporarily configured (e.g., by instructions or software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

E. Memory and Computer-Readable Media

Generally speaking, as used herein the phrase "memory" or "memory device" may refer to any system or device including computer-readable media ("CRM"), which may be any available media accessible by the relevant computing system for placing, keeping, and/or retrieving information (e.g., data, computer-readable instructions, program modules, etc). The CRM may be implemented in any technology, device, or group of devices included in the relevant computing system or in communication with the relevant computing system. The CRM may include volatile and/or non-volatile media, and removable and/or non-removable media. The CRM may include, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store information and which can be accessed by the computing system. The CRM may be communicatively coupled to a system bus, enabling communication between the CRM and other systems or components coupled to the system bus. In some implementations the CRM may be coupled to the system bus via a memory interface (e.g., a memory controller). A memory interface is a circuit that manages the flow of data between the CRM and the system bus.

F. System Bus(es)

Generally speaking, a processor or a particular system or subsystem may communicate with other components of the system or subsystem via one or more communication links. When communicating with components in a shared housing, for example, the processor may be communicatively connected to the components by a system bus. Unless stated otherwise, as used herein the phrase "system bus" refers to: a data bus (for carrying data), an address bus (for determining where the data should be sent), a control bus (for determining the operation to execute), or some combination thereof. Further, "system bus" may refer to any of several types of bus structures including a memory bus or memory controller, a peripheral bus, or a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

G. Data/Information Generation and Manipulation

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

H. Embodiments

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled,"

however, may also mean that two or more elements are not in direct contact with each other, but yet still co-operate or interact with each other. The embodiments are not limited in this context.

I. Relational and Logical Expressions

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

Although this detailed description contemplates various embodiments, it should be understood that the legal scope of the invention is defined by the words of the claims set forth at the end of this patent. This detailed description is to be construed as exemplary only and does not describe every possible embodiment, as describing every possible embodiment would be impractical, if not impossible. One could implement numerous alternate embodiments, using either current technology or technology developed after the filing date of this patent, which may fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims of this patent is referred to in this patent in a manner consistent with a single meaning, that is done for sake of clarity only so as to not confuse the reader, and it is not intended that such claim term be limited, by implication or otherwise, to that single meaning.

IX. Example Aspects

Embodiments of the techniques described in the present disclosure may include any number of the following aspects, either alone or combination:

1. A first system, comprising: (a) a controller configured to transmit to a display device display data representing a plurality of interfaces, the plurality of interfaces including: (i) a first interface that a user may interact with to select content assets to be presented when pages of an interactive multimedia pack ("IMP") are presented, and (ii) a second interface that a user may interact with to define a flow between one or more pages of the IMP; (b) one or more input devices coupled to the controller, wherein the controller is configured to receive from the one or more input devices: (i) first input data representing a content asset selected using the first interface, and (ii) second input data representing a flow-definition made using the second interface, the flow-definition including a first flow from a first page to a second page, a second flow from the first page to a third page, and one or more conditions for selecting a flow from the first flow and the second flow; (c) one or more memory devices coupled to the controller, the one or more memory devices storing: (i) first page data generated by the controller and representing the first page of the IMP, the first page data referencing the selected content asset; (ii) a record of rules generated by the controller according to the flow-definition represented by the second input data, the record of rules including the one or more conditions for selecting a flow from the first flow and the second flow; (d) one or more servers coupled to the one or more memory devices, the one or more servers configured to: (i) analyze the first page data to identify the selected content asset referenced by the first page data and to transmit to a client device the selected content asset for presentation by the client device of the first page; (ii) evaluate the one or more conditions included in the record of rules stored at the one or more memory devices; (iii) when the evaluation of the one or more conditions produces a first result: analyze second page data representing the second page to identify, and to transmit to the client device for presentation, content assets referenced by the second page data so that the client device can present the second page after the first page has been presented; and (iv) when the evaluation of the one or more conditions produces a second result: analyze third page data representing the third page to identify, and to transmit to the client device for presentation, content assets referenced by the third page data so that the client device can present the third page after the first page has been presented.

2. The first system of aspect 1, wherein the selected content asset represented by the first input data is an audio content asset; wherein the client device presents the first page by way of an interactive voice response presentation that includes a presentation of the audio content asset by way of a speaker of the client device.

3. The first system of aspect 1, wherein the selected content asset represented by the first input data is a visual content asset; wherein the client device presents the first page by way of a presentation that includes a presentation of the visual content asset by way of a screen of the client device.

4. The first system of aspect 3, wherein the visual content asset is an animation; wherein the first input data represents, for each of a plurality of points in time, a selection made via the first interface of: an image and a screen position for the selected image; wherein the selected images and screen positions for the plurality of points in time define the animation.

5. The first system of any of the previous aspects, wherein the first interface includes a timeline tool; wherein the selection made via the first interface is made using the timeline tool.

6. The first system of any of the previous aspects, wherein the plurality of interfaces further includes a third interface that a user may interact with to select a content asset to be presented when the page of the IMP is presented; wherein the controller is further configured to receive third input data; wherein the selected content asset represented by the first input data is one of an audio content asset or a visual content asset; wherein the selected content asset represented by the third input data is the other of the audio content asset and the visual content asset; wherein both the visual content asset and the audio content asset are transmitted to the client device for presentation of the first page.

7. The first system of aspect 6, wherein the controller is further configured to: when the first input data is received by the controller before the third input data is received by the controller: identify, from the received first input data, the first page as the page for which the selected visual content asset represented by the third input data has been selected.

8. The system of aspect 6, wherein the controller is further configured to: when the third input data is received by the controller before the first input data is received by the controller: identify, from the received third input data, the first page as the page for which the audio content asset represented by the first input data has been selected.

9. The first system of any of aspects 1-9, wherein the controller is further configured to: receive input data representing a selection of a visual representation displayed via the second interface; and identify the first page as the page associated with the selected visual representation; wherein the controller causes the first interface to be displayed so that one or more content assets may be selected for the identified first page.

10. The first system of any of aspects 1 or 3-5, wherein the selected content asset is a visual content asset; wherein the controller is further configured to transmit display data to the display device so that when received at the display device, the display device automatically performs one or more of the following: (i) displays via a third interface a design area for the identified first page so that an audio content asset can be selected for the first page via the third interface; or (ii) displays via the second interface a design area for the IMP so that a flow can be defined between a visual representation of the first page and one or more visual representations of one or more other pages.

11. The first system of any of aspects 1-3 or 6-9, wherein the selected content asset is an audio content asset; wherein the controller is further configured to transmit display data to the display device so that when received at the display device, the display device automatically performs one or more of the following: (i) displays via the first interface a design area for the identified first page so that a visual content asset can be selected for the first page via the first interface; and (ii) displays via the second interface a design area for the IMP, and displaying within the design area for the IMP a visual representation of the identified first page so that a flow can be defined between the visual representation of the first page and one or more visual representations of one or more other pages.

12. The system of aspect 1 or 3, wherein the selected content asset represents text, wherein presentation by the client device of the first page includes presentation of the text represented by the selected content asset via: (i) an electronic mail system, or (ii) a text messaging system.

13. The system of aspect 12, wherein the first input data representing the selected content asset is audio data received via a microphone, wherein the received audio is converted to the text.

14. The system of aspect 12, wherein the first input data representing the selected content asset is keystroke data received via a keyboard, wherein the text is identified from the received keystroke data.

15. The first system of any of aspects 1 or 3, wherein the selected content asset is an audio content asset and wherein the first interface includes a text entry area; wherein the controller is further configured to: (i) receive from the one or more input devices data representing text ("text data") that has been entered in the text entry area; (ii) convert the text data to audio data representing speech of the text; and (iii) store, at one or more memory devices, the audio data as the audio content asset.

16. The first system of any of the previous aspects, wherein the display data transmitted by the controller causes the display device to display the plurality of interfaces via simultaneous display of the first interface and the second interface such that they are each part of a single display.

17. The first system of any of aspects 1 or 3-8, wherein the first interface comprises: a design area and a library area; wherein the first input data further represents a selection of a visual content asset from the library area; wherein the controller is further configured to cause the display device to display in the design area the visual content asset that has been selected from the library area.

18. The first system of any of the previous aspects, wherein the display data transmitted by the controller causes the display device to display the second interface so that one or more visual representations of pages of the IMP are displayed, wherein a user may define connections between the visual representations of pages; wherein the received second input data includes: (i) data representing creation of a connection between a first visual representation of the first page and a second visual representation of the second page; (ii) data representing creation of a connection between the first visual representation of the first page and a third visual representation of the third page; and (iii) data representing a definition of the one or more conditions to be evaluated for selecting the second page as the next page after the first page or the third page as the next page after the first page.

19. A method comprising: (a) displaying, at a display device, a plurality of interfaces for editing pages of an interactive multimedia pack ("IMP") and for editing a flow between pages of the IMP, wherein displaying the plurality of interfaces includes: (i) displaying a first interface that a user may interact with to select content assets to be displayed when pages of the IMP are presented, and (ii) displaying a second interface that a user may interact with to define a flow between one or more pages of the IMP; (b) receiving at a controller and from one or more input devices: (i) first input data representing a content asset selected using the displayed first interface, and (ii) second input data representing a flow-definition made using the second interface, the flow-definition including a first flow from a first page to a second page, a second flow from the first page to a third page, and one or more conditions for selecting a flow from the first flow and the second flow; (c) generating by the controller: (i) first page data representing the first page of the IMP, said first page data referencing the selected content asset, and (ii) a record of rules including the one or more conditions for selecting a flow from the first flow and the second flow, said record of rules generated based on the flow-definition represented by the third input data; (d) after receiving a signal indicating that a client device will present the IMP: (i) analyzing the first page data to identify the selected content asset referenced by the first page data and transmitting to the client device the selected content asset for presentation by the client device of the first page; (ii) evaluating the one or more conditions included in the record of rules; (iii) when the evaluation of the one or more conditions produces a first result: analyzing second page data representing the second page to identify, and to transmit to the client device for presentation, one or more content assets referenced by the second page data so that the client device can present the second page after the first page has been presented, and (iv) when the evaluation of the one or more conditions produces a second result: analyzing third page data representing the third page to identify, and to transmit to the client device for presentation, one or more content assets referenced by the third page data so that the client device can present the third page after the first page has been presented.

20. The method of aspect 19, wherein the selected content asset represented by the first input data is an audio content asset; wherein the client device presents the first page by way of an interactive voice response presentation that includes a presentation of the audio content asset by way of a speaker of the client device.

21. The method of aspect 19, wherein the selected content asset represented by the first input data is a visual content asset; wherein the client device presents the first page by way of a presentation that includes a presentation of the visual content asset by way of a screen of the client device.

22. The method of aspect 19 or 20, wherein displaying the plurality of interfaces further includes: displaying a third interface that a user may interact with to select a content asset to be presented when the page of the IMP is presented; the method further including: receiving at the controller third input data representing a content asset selected using the displayed third interface; wherein the selected content asset represented by the first input data is one of an audio content asset or a visual content asset; wherein the selected content asset represented by the third input data is the other of the audio content asset and the visual content asset; the method further including analyzing the first page data to identify the audio content asset and the visual content asset referenced by the first page data and transmitting to the client device the audio content asset and the visual content asset for presentation by the client device of the first page.

23. The method of aspect 22, wherein the first input data is received by the controller before the third input data is received by the controller; and wherein the method further comprises: identifying, from the received first input data, the first page as the page for which the visual content asset represented by the third input data has been selected.

24. The method of any of aspects 19 or 21-23, wherein the selected content asset is a visual content asset; the method further comprising one or more of the following: (i) automatically displaying via a third interface a design area for the identified first page so that an audio content asset can be selected for the first page via the third interface; or (ii) automatically displaying via the second interface a visual representation of the identified first page so that a flow can be defined between the visual representation of the first page and one or more visual representations of one or more other pages.

25. The method of any of aspects 19, 20, 22, or 23, wherein the selected content asset is an audio content asset; the method further comprising one or more of the following: (i) automatically displaying via a third interface a design area for the identified first page so that a visual content asset can be selected for the first page via the third interface; or (ii) automatically displaying via the second interface a design area for the IMP, and displaying within the design area for the IMP a visual representation of the identified first page so that a flow can be defined between the visual representation of the first page and one or more visual representations of one or more other pages.

26. The method of any of aspects 19, 20, 22, 23, or 25, wherein the selected content asset is an audio content asset; wherein displaying the first interface comprises displaying a text entry area; wherein receiving first input data representing the selection via the first interface of the content asset for the first page comprises: receiving data representing text ("text data") entered in the text entry area; converting the text data to audio data representing speech of the text; and storing, at one or more memory devices, the audio data as the audio content asset.

27. The method of any of the previous aspects, wherein displaying the plurality of interfaces comprises: simultaneously displaying the first interface and the second interface such that they are each part of a single display.

28. The method of any of the previous aspects, wherein receiving from the one or more input devices: (i) first input data, and (ii) second input data comprises: receiving the second input data before receiving the first input data.

29. The method of any of aspects 19, 27, or 28, wherein the selected content asset is a visual content asset; wherein displaying the first interface comprises displaying a design area and a library area; wherein receiving the first input data comprises: receiving a selection of the visual content asset from the library area; and wherein the method further comprises displaying in the design area the visual content asset that has been selected from the library area.

30. The method of any of the previous aspects, wherein displaying the second interface comprises: displaying one or more visual representations of pages of the IMP, wherein a user may define connections between the visual representations of pages; and wherein receiving the second input data representing the definition, made via the second interface, of the flow between the one or more pages of the IMP further includes: (i) receiving data representing creation of a connection between a first visual representation of the first page and a second visual representation of the second page; (ii) receiving data representing creation of a connection between the first visual representation of the first page and a third visual representation of the third page; and (iii) receiving data representing a definition of the one or more conditions to be evaluated for selecting the second page as the next page or the third page as the next page.

31. A second system comprising: (a) a display device for displaying a plurality of interfaces for editing pages of an interactive multimedia pack ("IMP") and for editing a flow between pages of the IMP, wherein displaying the plurality of interfaces includes: (i) displaying a first interface to facilitate selection of a content asset to be presented when a page of the IMP is presented, and (ii) displaying a second interface to facilitate defining a flow between one or more pages of the IMP; (b) a means for receiving: (i) first input data representing a content asset selected using the displayed first interface, and (ii) second input data representing a flow-definition made using the displayed second interface, the flow-definition including a first flow from the first page to a second page, a second flow from the first page to a third page, and one or more conditions for selecting a flow from the first flow and the second flow; (c) a means for generating: (i) first page data representing a first page of the IMP, said first page data referencing the selected content asset, and (ii) a record of rules including the one or more conditions for selecting a flow from the first flow and the second flow, said record of rules generated based on the flow-definition represented by the third input data; (d) a means for performing the following after receiving a signal indicating that a client device will present the IMP: (i) transmitting the first page data to a client device so that the client device can present the first page in a manner that includes presenting the selected content asset referenced by the first page data; (ii) evaluating the one or more conditions included in the record of rules; (iii) when the evaluation of the one or more conditions produces a first result: transmitting second page data representing the second page to the client device so that the client device can present the second page after the first page has been presented, and (iv) when the evaluation of the one or more conditions produces a second result: transmitting third page data representing the third page so that the client device can present the third page after the first page has been presented.

32. The second system of aspect 31, wherein the means for receiving (i) first input data representing the content asset selected using the displayed first interface, and (ii) second input data representing the flow-definition made using the displayed second interface is one or more of: the IMP Authoring Tool 115, the audio interface 116, the visual interface 117, the flow interface 118, the controller 610, and/or the input device 639.

33. The second system of any of the previous aspects, wherein the means for generating (i) the first page data and (ii) the record of rules is one or more of: the IMP Authoring Tool 115, the audio interface 116, the visual interface 117, the flow interface 118, the rules engine 128, the controller 610, the input device 639, and/or one or more of the servers 620.

34. The second system of any of the previous aspects, wherein the means for transmitting the first page data to the client device is one or more of: the rules engine 128, the content provision unit 129, and/or one or more of the servers 620.

35. The second system of any of the previous aspects, wherein the means for evaluating the one or more conditions included in the record of rules is one or more of: the rules engine 128 and/or one or more of the servers 620.

36. The second system of any of the previous aspects, wherein the means for transmitting the second page data or third page data is one or more of: the rules engine 128, the content provision unit 129, and/or one or more of the servers 620.

The invention claimed is:

1. A system for facilitating authoring of an interactive multimedia pack, the system comprising:
   (a) a controller configured to transmit to a display device display data representing a plurality of interfaces to be simultaneously displayed for defining a flow between a plurality of pages of an interactive multimedia presentation ("IMP") that each include a plurality of content assets visual or audible in nature and for selecting the plurality of content assets for each of the pages, the plurality of interfaces including: (i) a first one or more interfaces that a user may interact with to select content assets to be presented when pages of the IMP are presented, and (ii) a second interface that a user may interact with to define the flow between the plurality of pages of the IMP;
   (b) one or more input devices coupled to the controller, wherein the controller is configured to receive from the one or more input devices: (i) first input data representing a plurality of content assets selected using the first one or more interfaces, and (ii) second input data representing a flow-definition made using the second interface, the flow-definition including a first flow from a first page to a second page representing a first version of a portion of the IMP, a second flow from the first page to a third page representing a second version of the portion of the IMP, and one or more conditions to be evaluated at run-time by a rules engine for selecting a flow from the first flow and the second flow based, at least in part, on the type of communication channel utilized to present the IMP;
   (c) one or more memory devices coupled to the controller, the one or more memory devices storing:
      (i) first page data generated by the controller and representing the first page of the IMP, the first page data referencing the selected content asset;
      (ii) a record of rules generated by the controller according to the flow-definition represented by the second input data, the record of rules including the one or more conditions for selecting a flow from the first flow and the second flow;
   (d) one or more servers coupled to the one or more memory devices, the one or more servers configured to:
      (i) analyze the first page data to identify the selected content asset referenced by the first page data and to transmit to a client device the selected content asset for presentation by the client device of the first page;
      (ii) evaluate the one or more conditions included in the record of rules stored at the one or more memory devices;
      (iii) when the evaluation of the one or more conditions produces a first result: analyze second page data representing the second page to identify, and to transmit to the client device for presentation, content assets referenced by the second page data so that the client device can present the second page after the first page has been presented; and
      (iv) when the evaluation of the one or more conditions produces a second result: analyze third page data representing the third page to identify, and to transmit to the client device for presentation, content assets referenced by the third page data so that the client device can present the third page after the first page has been presented.

2. The system of claim 1, wherein the selected content asset represented by the first input data is an audio content asset;
   wherein the client device presents the first page by way of an interactive voice response presentation that includes a presentation of the audio content asset by way of a speaker of the client device.

3. The system of claim 1, wherein the selected content asset represented by the first input data is a visual content asset;
   wherein the client device presents the first page by way of a presentation that includes a presentation of the visual content asset by way of a screen of the client device.

4. The system of claim 3, wherein the visual content asset is an animation;
   wherein the first input data represents, for each of a plurality of points in time, a selection made via the first one or more interfaces of: an image and a screen position for the selected image;
   wherein the selected images and screen positions for the plurality of points in time define the animation.

5. The system of claim 4, wherein the first one or more interfaces includes a timeline tool; wherein the selection made via the first one or more interfaces of the selected images and screen positions is made using the timeline tool.

6. The system of claim 1, wherein the first one or more interfaces includes visual interface and an audio interface that a user may interact with to select a content asset to be presented when the page of the IMP is presented;
   wherein the controller is further configured to receive third input data;
   wherein the selected content asset represented by the first input data is an audio content asset selected via the audio interface;

wherein the selected content asset represented by the third input data is a visual content asset selected via the visual interface;

wherein both the visual content asset and the audio content asset are transmitted to the client device for presentation of the first page.

7. The system of claim 6, wherein the controller is further configured to:

when the first input data is received by the controller before the third input data is received by the controller: identify, from the received first input data, the first page as the page for which the selected visual content asset represented by the third input data has been selected.

8. The system of claim 6, wherein the controller is further configured to:

when the third input data is received by the controller before the first input data is received by the controller: identify, from the received third input data, the first page as the page for which the audio content asset represented by the first input data has been selected.

9. The system of claim 1, wherein the controller is further configured to:

receive input data representing a selection of a visual representation displayed via the second interface; and identify the first page as the page associated with the selected visual representation;

wherein the controller causes the first one or more interfaces to be displayed so that one or more content assets may be selected for the identified first page.

10. The system of claim 1, wherein the selected content asset is a visual content asset;

wherein the controller is further configured to transmit display data to the display device so that when received at the display device, the display device automatically performs one or more of the following:

(i) displays via a third interface a design area for the identified first page so that an audio content asset can be selected for the first page via the third interface; or (ii) displays via the second interface a design area for the IMP so that a flow can be defined between a visual representation of the first page and one or more visual representations of one or more other pages.

11. The system of claim 1, wherein the selected content asset is an audio content asset;

wherein the controller is further configured to transmit display data to the display device so that when received at the display device, the display device automatically performs one or more of the following:

(i) displays via a third interface a design area for the identified first page so that a visual content asset can be selected for the first page via the third interface; and (ii) displays via the second interface a design area for the IMP, and displaying within the design area for the IMP a visual representation of the identified first page so that a flow can be defined between the visual representation of the first page and one or more visual representations of one or more other pages.

12. The system of claim 1, wherein the selected content asset represents text, wherein presentation by the client device of the first page includes presentation of the text represented by the selected content asset via: (i) an electronic mail system, or (ii) a text messaging system.

13. The system of claim 12, wherein the first input data representing the selected content asset is audio data received via a microphone, wherein the received audio is converted to the text.

14. The system of claim 12, wherein the first input data representing the selected content asset is keystroke data received via a keyboard, wherein the text is identified from the received keystroke data.

15. The system of claim 1, wherein the selected content asset is an audio content asset and wherein the first one or more interfaces includes a text entry area;

wherein the controller is further configured to:

(i) receive from the one or more input devices data representing text ("text data") that has been entered in the text entry area;

(ii) convert the text data to audio data representing speech of the text; and (iii) store, at one or more memory devices, the audio data as the audio content asset.

16. The system of claim 1, wherein the display data transmitted by the controller causes the display device to display the plurality of interfaces via simultaneous display of the first one or more interfaces and the second interface such that they are each part of a single display.

17. The system of claim 1, wherein the first one or more interfaces comprises:

a design area and a library area;

wherein the first input data further represents a selection of a visual content asset from the library area;

wherein the controller is further configured to cause the display device to display in the design area the visual content asset that has been selected from the library area.

18. The system of claim 1, wherein the display data transmitted by the controller causes the display device to display the second interface so that one or more visual representations of pages of the IMP are displayed, wherein a user may define connections between the visual representations of pages;

wherein the received second input data includes:

(i) data representing creation of a connection between a first visual representation of the first page and a second visual representation of the second page;

(ii) data representing creation of a connection between the first visual representation of the first page and a third visual representation of the third page; and (iii) data representing a definition of the one or more conditions to be evaluated for selecting the second page as the next page after the first page or the third page as the next page after the first page.

19. A method comprising:

(a) simultaneously displaying, at a display device, a plurality of interfaces for defining a flow between a plurality of pages of an interactive multimedia presentation ("IMP") that each include a plurality of content assets visual or audible in nature and for selecting the plurality of content assets for each of the pages, wherein displaying the plurality of interfaces includes:

(i) displaying a first one or more interfaces that a user may interact with to select content assets to be presented when a page of the IMP is presented, and (ii) displaying a second interface that a user may interact with to define a flow between one or more pages of the IMP;

(b) receiving at a controller and from one or more input devices: (i) first input data representing a content asset selected using the displayed first one or more interfaces, and (ii) second input data representing a flow-definition made using the second interface, the flow-definition including a first flow from a first page to a second page representing a first version of a portion of the IMP, a second flow from the first page to a third page representing a second version of the portion of the IMP, and one or more conditions to be evaluated at run-time by a rules engine for selecting a flow from the first flow and the second flow based, at least in part, on the type of communication channel utilized to present the IMP;

(c) generating by the controller: (i) first page data representing the first page of the IMP, said first page data referencing the selected content asset, and (ii) a record of rules including the one or more conditions for selecting a flow from the first flow and the second flow, said record of rules generated based on the flow-definition represented by the third input data;

(d) after receiving a signal indicating that a client device will present the IMP:
  (i) analyzing the first page data to identify the selected content asset referenced by the first page data and transmitting to the client device the selected content asset for presentation by the client device of the first page;
  (ii) evaluating the one or more conditions included in the record of rules;
  (iii) when the evaluation of the one or more conditions produces a first result: analyzing second page data representing the second page to identify, and to transmit to the client device for presentation, one or more content assets referenced by the second page data so that the client device can present the second page after the first page has been presented, and
  (iv) when the evaluation of the one or more conditions produces a second result: analyzing third page data representing the third page to identify, and to transmit to the client device for presentation, one or more content assets referenced by the third page data so that the client device can present the third page after the first page has been presented.

20. The method of claim 19, wherein the selected content asset represented by the first input data is an audio content asset;
wherein the client device presents the first page by way of an interactive voice response presentation that includes a presentation of the audio content asset by way of a speaker of the client device.

21. The method of claim 19, wherein the selected content asset represented by the first input data is a visual content asset;
wherein the client device presents the first page by way of a presentation that includes a presentation of the visual content asset by way of a screen of the client device.

22. The method of claim 21, wherein the visual content asset is text;
wherein the client device presents the first page by way of a presentation that includes presenting the text by way of (i) an electronic mail system, or (ii) a text messaging system.

23. The method of claim 19, wherein displaying the plurality of interfaces further includes: displaying a third interface that a user may interact with to select a content asset to be presented when the page of the IMP is presented;
the method further including: receiving at the controller third input data representing a content asset selected using the displayed third interface;

wherein the selected content asset represented by the first input data is an audio content asset;
wherein the selected content asset represented by the third input data is a visual content asset;
the method further including analyzing the first page data to identify the audio content asset and the visual content asset referenced by the first page data and transmitting to the client device the audio content asset and the visual content asset for presentation by the client device of the first page.

24. The method of claim 23, wherein the first input data is received by the controller before the third input data is received by the controller; and
wherein the method further comprises: identifying, from the received first input data, the first page as the page for which the visual content asset represented by the third input data has been selected.

25. The method of claim 24, wherein the selected content asset is a visual content asset;
the method further comprising one or more of the following:
  (i) automatically displaying via a third interface a design area for the identified first page so that an audio content asset can be selected for the first page via the third interface; or
  (ii) automatically displaying via the second interface a visual representation of the identified first page so that a flow can be defined between the visual representation of the first page and one or more visual representations of one or more other pages.

26. The method of claim 24, wherein the selected content asset is an audio content asset;
the method further comprising one or more of the following:
  (i) automatically displaying via a third interface a design area for the identified first page so that a visual content asset can be selected for the first page via the third interface; or
  (ii) automatically displaying via the second interface a design area for the IMP, and displaying within the design area for the IMP a visual representation of the identified first page so that a flow can be defined between the visual representation of the first page and one or more visual representations of one or more other pages.

27. The method of claim 19, wherein the selected content asset is an audio content asset;
wherein displaying the first one or more interfaces comprises displaying a text entry area;
wherein receiving first input data representing the selection via the first one or more interfaces of the content asset for the first page comprises:
  (i) receiving data representing text ("text data") entered in the text entry area;
  (ii) converting the text data to audio data representing speech of the text; and
  (iii) storing, at one or more memory devices, the audio data as the audio content asset.

28. The method of claim 19, wherein displaying the plurality of interfaces comprises:
simultaneously displaying the first one or more interfaces and the second interface such that they are each part of a single display.

29. The method of claim 19, wherein receiving from the one or more input devices: (i) first input data, and (ii) second input data comprises:

receiving the second input data before receiving the first input data.

30. The method of claim 19, wherein the selected content asset is a visual content asset;
- wherein displaying the first one or more interfaces comprises displaying a design area and a library area;
- wherein receiving the first input data comprises: receiving a selection of the visual content asset from the library area; and
- wherein the method further comprises displaying in the design area the visual content asset that has been selected from the library area.

31. The method of claim 19, wherein displaying the second interface comprises:
- displaying one or more visual representations of pages of the IMP, wherein a user may define connections between the visual representations of pages; and
- wherein receiving the second input data representing the definition, made via the second interface, of the flow between the one or more pages of the IMP further includes:
  - (i) receiving data representing creation of a connection between a first visual representation of the first page and a second visual representation of the second page;
  - (ii) receiving data representing creation of a connection between the first visual representation of the first page and a third visual representation of the third page; and
  - (iii) receiving data representing a definition of the one or more conditions to be evaluated for selecting the second page as the next page or the third page as the next page.

* * * * *